US010829733B2

United States Patent
Tryggvason et al.

(10) Patent No.: US 10,829,733 B2
(45) Date of Patent: *Nov. 10, 2020

(54) COMPOSITION AND METHOD FOR ENABLING PROLIFERATION OF PLURIPOTENT HUMAN STEM CELLS

(75) Inventors: Karl Tryggvason, Djursholm (SE); Sergey Rodin, Stockholm (SE); Anna Domogatskaya, Rönninge (SE)

(73) Assignee: BIOLAMINA AB, Sundbyberg (SE)

( * ) Notice: Subject to any disclaimer, the term of this patent is extended or adjusted under 35 U.S.C. 154(b) by 242 days.

This patent is subject to a terminal disclaimer.

(21) Appl. No.: 12/725,877

(22) Filed: Mar. 17, 2010

(65) Prior Publication Data

US 2010/0203635 A1    Aug. 12, 2010

Related U.S. Application Data

(63) Continuation-in-part of application No. 11/969,620, filed on Jan. 4, 2008.

(60) Provisional application No. 60/883,406, filed on Jan. 4, 2007.

(51) Int. Cl.
*C12N 5/0735* (2010.01)

(52) U.S. Cl.
CPC ........ *C12N 5/0606* (2013.01); *C12N 2500/25* (2013.01); *C12N 2500/90* (2013.01); *C12N 2500/98* (2013.01); *C12N 2501/115* (2013.01); *C12N 2501/998* (2013.01); *C12N 2533/52* (2013.01)

(58) Field of Classification Search
CPC .............. C12N 5/0606; C12N 2533/52; C12N 2501/115; C12N 2501/998; C12N 2500/99
USPC ................................................. 435/366, 402
See application file for complete search history.

(56) References Cited

U.S. PATENT DOCUMENTS 7,217,569 B2 *   5/2007   Thomson ....................... 435/377
2003/0187226 A1 * 10/2003   Goodey ........... C07K 14/70571
                                                                530/362
2008/0213885 A1   9/2008   Tryggvason et al.

FOREIGN PATENT DOCUMENTS

WO    WO 2008084401       7/2008
WO    WO 2011/110886 A1   9/2011

OTHER PUBLICATIONS

Lim et al. Proteomics, 2:1187-1203, 2002.*
Mallon et al. The Int. J. of Biochem. & Cell Bio., 38: 1063-1075, 2006.*
R&D systems, http://www.rndsystems.com/product_detail_objectname_neural_stem_cells.aspx, "neural stem cells" accessed online on Jan. 11, 2012, pp. 1-2.*
Gilmore et al., Experimental Hematology, 28: 1297-1305, 2000.*
Li et al., Cardiovascular Research Advance Access, pp. 1-9, Aug. 21, 2010.*
Thomson. Science, 282: 1145-1147, 1998.*
Beattie et al. Stem Cells, 23: 489-495, 2005.*
Millipore catalog, accessed online at http://www.millipore.com/, publication date, May 30, 2005.*
Kikkawa et al., Experimental Cell Res., 300: 94-108, 2004.*
Doi et al., J. of Biological Chemistry., 15(12): 12741-12748, 2002.*
Humphrey et al., Stem Cells, 22: 522-530, 2004.*
Abeyta et al., Human Molecular Genetics, 13(6): 601-608, 2004.*
Ludwig et al., Nature Biotechnology24(2): 185-187, 2006, Supplementary Methods only, pp. 1-5.*
Evseenko et al., "Identification of the critical extracellular matrix proteins that promote human embryonic stem cell assembly", Stem Cells and Development, vol. 18, No. 6, Jul. 2009, pp. 919-927.
Domogatskaya, Anna et al., "Laminin-511 but No. -322, -111, or -411 enables mouse embryonic stem cell self-renewal in vitro" Stem Cells, Alphamed Press LNKD-DOI: 10.1634/Stemcells. 2007-0389, vol. 26, No. 11. pp. 2800-2809.
Meng Guoliang, et al., A novel method for generating xeno-free human feeder cells for human embryonic stem cell culture: Stem Cells and Development, Elsevier, NL LNKD-DOI:10.1089/SCD. 2007.0236, vol. 17, No, 3. pp. 413-422.
Ludwig, T. E., et al., "Derivation of human embryonic stem cells in defined conditions" Nature Biotechnology, Feb. 2006 Nature Publishing Group US, vol. 24, No. 2. pp. 185-187.
Miyazaki, T., et al., "Recombinant human laminin isoforms can support the undifferentiated growth of human embryonic stem cells" Biochemical and Biophysical Research Communications, Academic Press Inc., Orlando, FL, US LNKD-DOI:10.1016/J.BBRC. 2008.07.111, vol. 375, No. 1. pp. 27-32.
Rodin, Sergey, et al., "Long-term self-renewal of human pluripotent stem cells on human recombinant laminin-511." Nature Biotechnology, Jun. 2010 LNKD-PUBMED: 20512123, vol. 28, No. 7. pp. 611-615.
International Search Report dated Jun. 30, 2010.
Domogatskaya et al.; Laminin-511 but Not—332, -111, or -411 Enables Mouse Embryonic Stem Cell Self-Renewal In Vitro; Stem Cells; vol. 26; pp. 2800-2809; 2008.
Hashimoto et al.; Regulation of Proliferation and Chondrogenic Differentiation of Human Mesenchymal Stem Cells by Laminin-5 (Laminin-332); Stem Cells; vol. 24; pp. 2346-2354; 2006.

(Continued)

*Primary Examiner* — Thaian N. Ton
(74) *Attorney, Agent, or Firm* — Fay Sharpe LLP

(57) ABSTRACT

Compositions and processes for culturing human stem cells in vitro in an undifferentiated state are disclosed. In this regard, human embryonic stem cells proliferated and maintained their pluripotency when cultured on plates coated with recombinant laminin-10 (laminin-511).

11 Claims, 15 Drawing Sheets

Specification includes a Sequence Listing.

(56) References Cited

OTHER PUBLICATIONS

Miyazaki et al.; Recombinant human laminin isoforms can support the undifferentiated growth of human embryonic stem cells; Biochemical and Biophysical Research Communications; vol. 375; pp. 27-32; 2008.
Rodin et al.; Long-term self-renewal of human pluripotent stem cells on human recombinant laminin-511; Nature Biotechnology; vol. 28; No. 6; pp. 611-615; 2010.
Extended European Search Report for EP Application No. 16000633.4 dated Jun. 27, 2016.

* cited by examiner

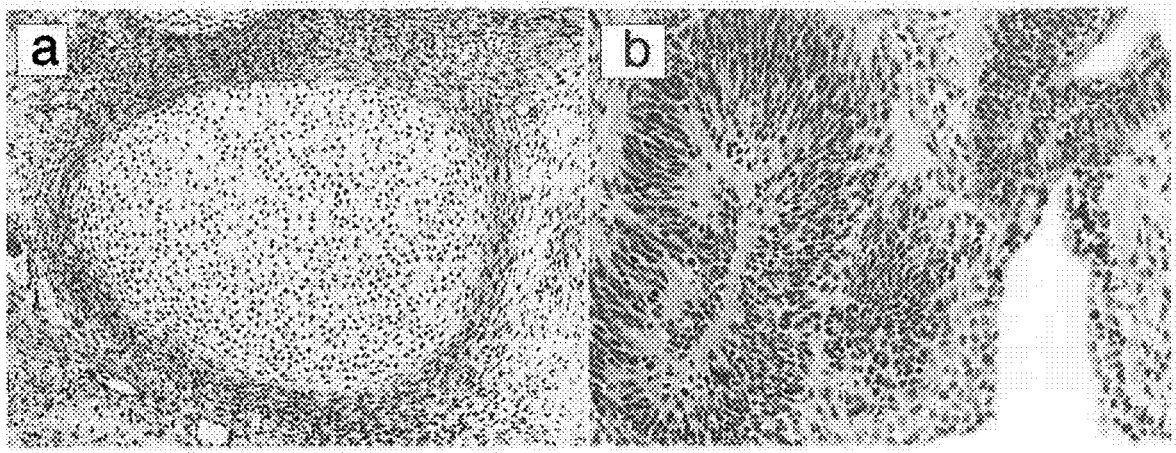
Fig. 7aFig. 7b
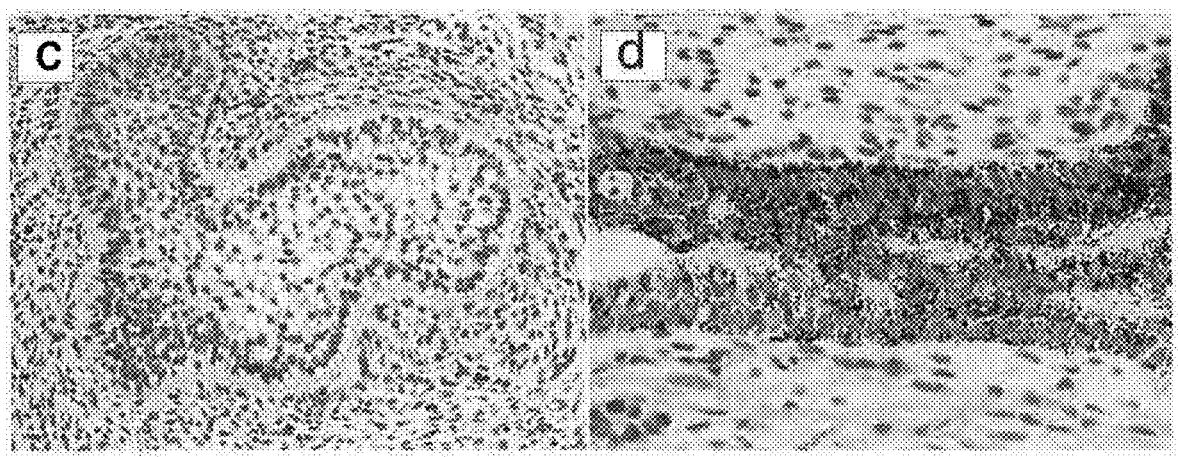
Fig. 7cFig. 7d

COMPOSITION AND METHOD FOR ENABLING PROLIFERATION OF PLURIPOTENT HUMAN STEM CELLS

CROSS REFERENCE TO RELATED APPLICATIONS

This application is a continuation-in-part of U.S. patent application Ser. No. 11/969,620, filed Jan. 4, 2008, which claimed priority to U.S. Provisional Application Ser. No. 60/883,406, filed on Jan. 4, 2007.

All of these applications are fully incorporated herein by reference in their entirety.

BACKGROUND

The present disclosure relates, in various exemplary embodiments, generally to compositions and methods for enabling adhesion, proliferation and self-renewal maintenance of pluripotent, or undifferentiated, human stem cells grown in vitro. These human stem cells include embryonic stem cells, bone marrow stem cells, and pluripotent stem cells.

A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics. (Skottman, H., Dilber, M. S., and Hovatta, O. (2006); The derivation of clinical-grade human embryonic stem cell lines; FEBS Lett 580, 2875-2878).

Human embryonic cells require feeder cells for maintenance in a pluripotent state in vitro or differentiation inhibitors like Noggin and/or high doses of basic fibroblast growth factor (FGF) when cultured on Matrigel™ (see for review: Skottman, H., Dilber, M. S., and Hovatta, O. (2006); The derivation of clinical-grade human embryonic stem cell lines; FEBS Lett 580, 2875-2878). However, the use of feeder cells has a number of drawbacks. For example, feeder cells can contain pathogens, such as viruses that can infect the stem cells (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

Feeder-free systems that support human embryonic stem cell self-renewal require either i) Matrigel™ (Richards, M., Fong, C. Y., Chan, W. K., Wong, P. C., and Bongso, A. (2002); Human feeders support prolonged undifferentiated growth of human inner cell masses and embryonic stem cells; Nat Biotechnol 20, 933-936); (Xu, C., Inokuma, M. S., Denham, J., Golds, K., Kundu, P., Gold, J. D., and Carpenter, M. K. (2001); Feeder-free growth of undifferentiated human embryonic stem cells; Nat Biotechnol 19, 971-974); (Xu, R. H., Peck, R. M., Li, D. S., Feng, X., Ludwig, T., and Thomson, J. A. (2005); Basic FGF and suppression of BMP signaling sustain undifferentiated proliferation of human ES cells; Nat Methods 2, 185-190); or, ii) mouse feeders-derived extracellular matrix (Klimanskaya, I., Chung, Y., Meisner, L., Johnson, J., West, M. D., and Lanza, R. (2005); Human embryonic stem cells derived without feeder cells; Lancet 365, 1636-1641) as adhesive substrata. However, these coatings are of xenogenic origin and therefore cannot be used in clinics according to FDA requirements (Hovatta, O., and Skottman, H. (2005); Feeder-free derivation of human embryonic stem-cell lines; Lancet 365, 1601-1603). These coatings also fail to fulfill criteria of defined system and non-immunogenicity, importance of which is discussed in (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

Due to the problems described above, the development of chemically defined and xeno-free culture environments for human embryonic stem (hES) cells has been an important goal. In this regard, search for substrata for expansion of hES cells has been particularly important. Extracellular matrix (ECM) proteins, particularly basement membrane (BM) components, constitute an important part of in vivo niches for differentiation, phenotype maintenance and function of many types of somatic and stem cells in the human body and, therefore, have a potential for self-renewal of certain cell types. Among basement membrane proteins, laminins have been shown to influence cellular differentiation, adhesion, proliferation, and migration.

During mammalian embryonic development, a fertilized oocyte first divides into two cells, followed by another cell duplication to generate a four-cell embryo. At the four-cell stage, the embryonic cells are bound together with the help of cell membrane proteins and also the molecules of a new connective tissue (extracellular matrix). The first extracellular matrix molecules to appear are basement membrane proteins, such as laminin and proteoglycan. Subsequently, the embryonic cells start to differentiate into the three germ cell layers; ectoderm, endoderm and mesoderm, with initiation of morphogenesis. The extracellular matrix molecules, such as laminins are responsible for interactions with cell surface receptors, thus regulating cell behavior such as adhesion, proliferation, migration and differentiation (Colognato, H., and Yurchenco, P. D. (2000); Form and function: the laminin family of heterotrimers; Dev Dyn 218, 213-234), while other extracellular matrix components such as collagens of types I, II, III or IV primarily serve a mechanical supportive function (Aumailley, M., and Gayraud, B. (1998); Structure and biological activity of the extracellular matrix; J Mol Med 76, 253-265).

Laminins are large trimeric extracellular matrix proteins that are composed of alpha, beta, and gamma chains. There exist five different alpha chains, three beta chains and three gamma chains that in human tissues have been found in at least fifteen different combinations (Colognato, H., and Yurchenco, P. D. (2000); Form and function: the laminin family of heterotrimers; Dev Dyn 218, 213-234); (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332). These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains (laminin nomenclature: (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332)).

The laminin isoforms exhibit varying spatio-temporal expression patterns, as well as tissue specific locations and functions. Thus, LN-211 is primarily present in BMs of muscle cells and motor neuron synapses, while LN-111 is restricted to the early embryo and later to certain epithelial cells. LN-332 is specifically found in subepithelial BMs and LN-411 is located in subendothelial BMs. LN-511 is ubiquitously distributed and has been found in BMs of the early embryo and BMs of most adult tissues. Mutations in many laminin chains result in severe diseases, such as junctional epidermolysis bullosa ($\alpha 3$, $\beta 3$, $\gamma 2$ chains) and congenital muscular dystrophy ($\alpha 2$ chain), nephrotic syndrome ($\beta 2$ chain), capillary disorders ($\alpha 4$ chain), which demonstrates their crucial functional role for cell lineages in specific tissues. Deletion of the genes for the ubiquitous $\alpha 5$, $\beta 1$, and $\gamma 1$ chains cause lethality in mice, which emphasizes their essential role for development of the organisms.

Laminins are the first ECM proteins cells to be identified in the early embryo, and laminin chains have been detected on the cell surface at the 2-cell stage in mouse embryos. The inner cell mass of blastocysts, which are a natural origin of ES cells, has been shown to comprise the laminin $\alpha 5$ chain.

There are numerous studies in which the ECM proteins have been used as coating substrata for hES cultures in vitro, but in those cases either undefined mixtures of ECM proteins or undefined media were used, or the experiments were not carried out long enough with all necessary assays made. Thus far, the most successful feeder cell free coating material used for hES cell cultures is Matrigel, a complex tumor and BM-like extract obtained from murine Engelbreth-Holm-Swarm (EHS) sarcoma tumor tissues. Matrigel mainly contains murine LN-111, type IV collagen, perlecan and nidogen, but also varying amounts of other materials, including growth factors and cellular proteins and, therefore, its composition is undefined and varies from batch-to-batch. This variability can cause irreproducibility of scientific results, and due to the animal origin of the substratum makes Matrigel unacceptable for the expansion and maintenance of hES cells for human cell therapy.

Most laminin isoforms are difficult or impossible to extract and purify in native forms from tissues due to extensive crosslinking between ECM proteins, and they can only be produced in minute amounts from cells such as keratinocytes and endothelial cells. Only recently, laminins such as LN-332, LN-411 and LN-511 have been successfully produced as human recombinant proteins.

Notwithstanding the above, there continues to be a need for providing compositions and methods for culturing and growing human embryonic stem cells. In this regard, providing compositions and methods for enabling the proliferation and survival of pluripotent human stem cells in vitro without use of differentiation inhibitory agents such as LIF or feeder cells would be advantageous.

SUMMARY

The present disclosure is directed to the development of compositions, such as extracellular matrices, and processes for using the same, for culturing human stem cells in vitro in an undifferentiated state.

It has been found that certain laminins provide a defined and suitable extracellular matrix for the growth and proliferation of undifferentiated human embryonic stem cells in vitro. This is absent from feeder cells and/or differentiation inhibitors, or in other words feeder cells and/or differentiation inhibitors are not necessary for the embryonic stem cells to grow and proliferate on the laminin extracellular matrix. Also, it has been found that when pluripotent human embryonic stem cells are cultured on plates coated with recombinant laminin-10 (laminin-511) in a chemically defined medium, such as an analog of mTeSR1, the cells can proliferate and maintain their pluripotency even in an absence of differentiation inhibitors. As used herein, the term "chemically defined" refers to a medium of which all the ingredients are known, the quantity (absolute or relative) of each ingredient is known, and the medium does not contain any plant or animal tissue.

Also, a system was established that was completely devoid of animal products or feeder cells and contained only one undefined component, ≥96% pure human albumin, by culturing different hES cell lines on human recombinant laminin-511 that is a natural hES cell niche. The hES cells self-renewed with normal karyotype for at least 4 months (20 passages), after which the cells could develop teratomas containing cell lineages of all three germ layers. When plated on laminin-511 in small clumps hES cells spread out in a monolayer, maintaining cellular homogeneity with approximately 97% Oct-4-positive cells. Adhesion of hES cells was dependent on $\alpha 6\beta 1$ integrin. The use of homogeneous monolayer hES cell cultures provides more controllable conditions for design of differentiation pathways for stem cells. This xeno-free and feeder-free system may be useful for the development of cell lineages for cell therapy purposes.

These and other non-limiting features of the present disclosure are discussed in more detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIG. 4 demonstrates adhesion of human ES cells to different coatings and expression of laminin chains in hES cells.

FIG. 5 demonstrates integrin receptors on hES cell surface and their role in adhesion to LN-511.

FIG. 6 shows representative immunostaining analysis, RT-PCR, FACS analysis, real-time quantitative RT-PCR and quantitative Western blot analysis of HS207 cultured on LN-511 in O3 medium and free from any animal derived components H3 medium.

FIG. 7 demonstrates the pluripotency of HS207 cells after extensive passaging on LN-511. Teratomas composed of tissue components of the three germ layers were formed after subcutaneous injection into SCID mice of H5207 cells after culture of 15 passages on LN-511. FIG. 7a shows cartilage, HE-staining. Magnification ×100. FIG. 7b shows developing neural tissue and intestinal endoderm, the goblet cells shown in red, HE-PAS staining. Magnification: ×400. FIG. 7c shows developing kidney glomerulus, HE staining. Magnification: ×400. FIG. 7d shows retinal pigment epithelium, HE staining. Magnification: ×400.

FIG. 8 shows H1 and H9 cells after 5 passages (1 month) on LN-511 in O3 medium expressed markers of pluripotency Oct4 (green), Nanog (green), and Sox2 (red). DAPI staining is in blue. Magnification: ×20.

FIG. 13 is a set of pictures showing early stages of derivation of the hESC line HS588 on LN511 in O3 medium.

DETAILED DESCRIPTION

Compositions and processes for culturing human stem cells in vitro in an undifferentiated state are disclosed. In this regard, human embryonic stem cells proliferated and maintained their pluripotency when cultured on plates coated with recombinant laminin-10 (laminin-511).

Expression of cytokines, cell cycle regulation and mechanisms of self-renewal are different in human and mouse ES cells. For instance, STAT3 activation is sufficient for self-renewal of mouse ES cells but cannot prevent differentiation of hES cells. Therefore, any results obtained with mouse ES cells cannot be directly extrapolated to human ones.

Recently, a feeder-free and xeno-free hES cell culture system has been reported. It contains human albumin purified from plasma and a human protein mixture for culture dish coating. The human proteins cell culture dish coating is reported to contain IV collagen, vimentin, fibronectin and human laminin, which has been shown to be a mixture of degraded proteins from human placenta. It contains fragments of several laminin types and frequently also other BM proteins and fibronectin. Therefore, these hES cell conditions are variable, cannot be considered chemically defined, and the component(s) of the matrix providing self-renewal are unknown.

In the present disclosure, Applicants explored whether human recombinant LN-511 alone can support self-renewal of hES cells in culture for long periods of time. Applicants cultured hES cell lines HS420, HS207 and HS40133 on culture dishes precoated with human recombinant LN-511 produced in human embryonic kidney cells (HEK293). Two different culture media, O3 and H3, were used. The O3 medium was a variant of the commercially available chemically defined mTeSR1 medium with bovine serum albumin as the only animal derived component. The H3 medium was a variant of chemically defined and xeno-free TeSR1 medium containing human serum albumin. In order to decrease potential batch-to-batch variability of the human albumin used, Applicants dialyzed the protein solution using 12-14 KDa dialysis membranes. To passage cells free from any animal-derived components, TrypLE™ Express enzyme was used. Control cells were cultured on Matrigel in O3 medium or on a layer of feeder cells in a serum replacement based medium. Applicants studied the adhesion of hESC cells to different ECM proteins. LN-511 provided the largest cell contact areas with the substratum. Human induced pluripotent stem (iPS) cell lines also self-renewed on LN-511. The adhesion was dependent on α6β1 integrin, which has been showed to be most abundant on hES cell surfaces. LN-511 was expressed in hES cells and as a part of hES cell environment in feeder-dependent cell cultures and in the early embryo could be a natural substratum for hES cell adhesion, migration and proliferation.

Figure 1:
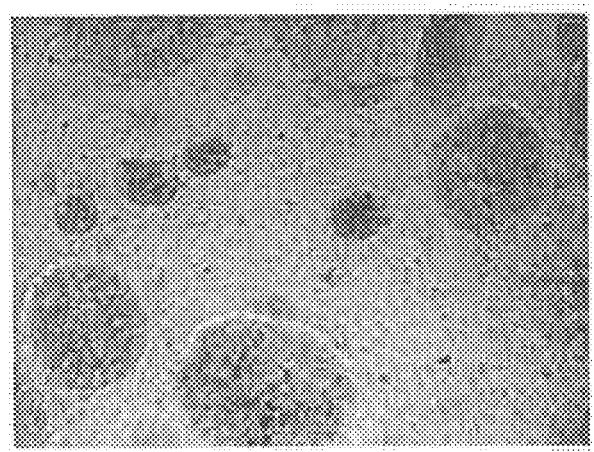
FIG. 1 is a microphotograph (phase contrast) of human embryonic stem cells on plates coated with recombinant laminin-10 (laminin-511) in a chemically defined medium after 105 days of feeder-free culturing.
Figure 2:
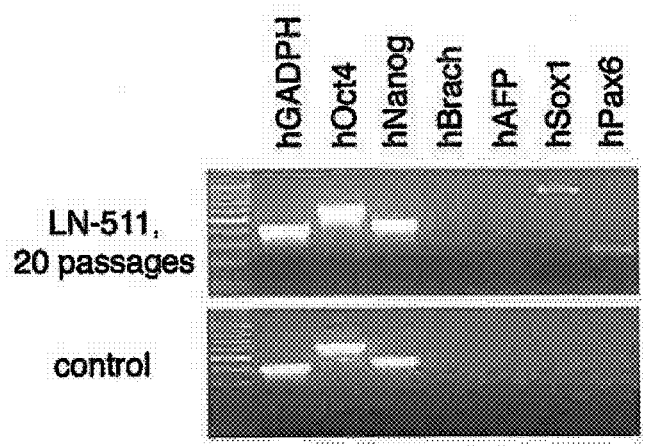
FIG. 2 is a photograph of RT-PCR showing the expression of pluripotency markers (Oct4, Nanog), internal control (GAPDH) and differentiation markers (alpha-fetoprotein, brachyury, Sox1 and Pax6) in human embryonic stem cells cultured on laminin-10 (laminin-511) in the chemically defined medium for 105 days (LN-511, 20 passages) and on human foreskin fibroblasts (control) in the conventional medium. Here, hGADPH, hOct4, hNanog, hBrach, hAFP, hSox1 and hPax6 stand for GAPDH, Oct4, Nanog, brachyury, alpha-fetoprotein, Sox1 and Pax6, respectively.
Figure 3:
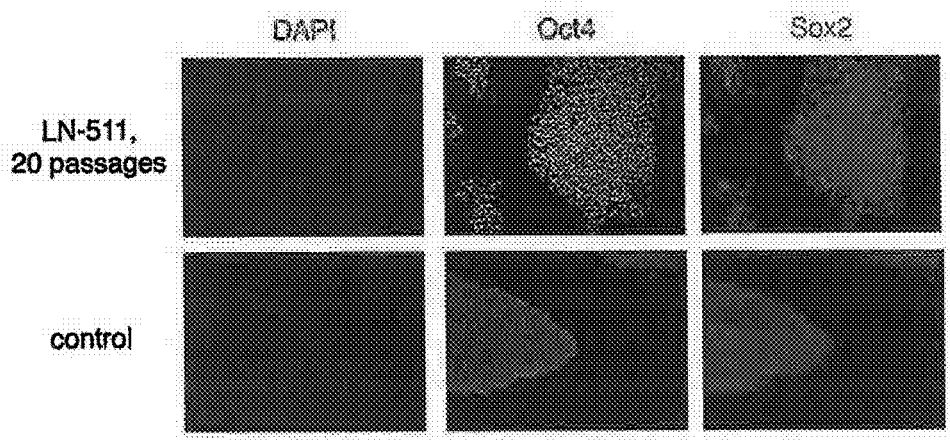
FIG. 3 contains a series of color microphotographs (immunofluorescence) demonstrating human embryonic stem cell self-renewal effect on laminins-511. After culturing on laminin-511 in the chemically defined media for 105 days (20 passages), human embryonic stem cells continue to express pluripotency markers Oct4 (green) and Sox2 (red) (LN-511, 20 passages). Human embryonic stem cells cultured on human foreskin fibroblasts in the conventional medium also express pluripotency markers Oct4 and Sox2 (control).

It was also found that when pluripotent human embryonic stem cells are cultured on plates coated with recombinant human laminin-10 (laminin-511) in chemically defined medium, the cells proliferate and maintain their pluripotency for at least 105 days (20 passages) (FIGS. 1-3). Expression of pluripotency markers, such as Oct4, Sox2 and Nanog, and the proliferation rate, also remained stable.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

The present disclosure will further be illustrated in the following non-limiting two sets of working examples, it being understood that these examples are intended to be illustrative only and that the disclosure is not intended to be limited to the materials, conditions, process parameters and the like recited herein. All proportions are by weight unless otherwise indicated.

I. Methods for First Set of Experiments

Cell Culture

Human embryonic stem cells (two lines were used: HS420 and HS207, both kindly provided by Prof. Hovatta, Karolinska University Hospital Huddinge, Karolinska Institute, Sweden) were cultured on plates coated with recombinant laminin-10 (laminin-511) in the chemically defined medium, analog of mTeSR1. The medium was prepared as described in (Ludwig, T. E., Bergendahl, V., Levenstein, M. E., Yu, J., Probasco M. D. and Thomsom, J. A. (2006); Feeder-independent culture of human embryonic stem cells; Nat Methods 8, 637-646) with several exceptions. Firstly, recombinant human FGF basic (R@DSystems) was used instead of zbFGF and albumin from bovine serum (SIGMA-Aldrich, B4287) was used instead of BSA fraction V. Secondly, Insulin-Transferrin-Selenium Supplement (Invitrogen) added in already made medium was used as a source of the elements instead of the method described in the article. The human embryonic stem cells were passages in clumps at 4-6 days intervals by exposure to TrypLE™ Express (GIBCO). The cells were subjected to the enzyme for 2 minutes at room temperature, then washed 2 times with the medium, followed by gentle scraping to collect. Big clumps of the cells were broken by gentle pipetting and 1:3 passaged.

Control human embryonic stem cells were maintained on human foreskin fibroblasts in the conventional medium as described in (Inzunzaa, J., Gertow, K., Strömberg, M., A., Matilainen, E., Blennow, E., Skottman, H., Wolbank, S., Åhrlund-Richter, L. and Hovatta, O. (2005); Derivation of Human Embryonic Stem Cell Lines in Serum Replacement Medium Using Postnatal Human Fibroblasts as Feeder Cells. Stem Cells 2005; 23:544-549). The cells were mechanically passaged by cutting the colony to eight pieces using a scalpel under the stereo microscope. Mechanical splitting was carried out at 6-day intervals. Nondifferentiated cells, as judged by morphology, were chosen for each further passage.

Plate Coating 96-well tissue cell culture plates (Sarstedt) were coated overnight at 4° C. by sterile solutions of extracellular matrix proteins: murine laminin-111 (Invitrogen), human recombinant laminin-332, human recombinant laminin-411 (Kortesmaa, J., Yurchenco, P., and Tryggvason, K. (2000); Production, purification, and interactions with integrins. J Biol Chem 275, 14853-14859, U.S. Pat. No. 6,638,907), human recombinant laminin-511 (Doi, M., Thyboll, J., Kortesmaa, J., Jansson, K., Iivanainen, A., Parvardeh, M., Timpl, R., Hedin, U., Swedenborg, J., and Tryggvason, K. (2002); Production, purification, and migration-promoting activity on vascular endothelial cells. J Biol Chem 277, 12741-12748; U.S. Pat. No. 6,933,273), all in concentration 30 ug/ml (5 ug/mm$^2$), growth factor-depleted Matrigel™ (1:30)

(BD Biosciences), bovine gelatin 1 mg/ml (Sigma), 0.1 mg/ml poly-D-lysine (Sigma).

Cell Adhesion Assays

Attachment assay was performed as described ([Extracellular Matrix Protocols, 2000). Briefly, MaxiSorp 96-well plates (Nunc) coated by extracellular matrix proteins as described above and blocked by 1% heat-denatured BSA solution. Undifferentiated embryonic cells were plated at cell density of 800 cell/mm$^2$ upon extracellular matrix-coated plates and were left to adhere for 1 hour at 37° C. Non-adherent cells were washed away, and adherent cells were fixed for 20 min by 5% glutaraldehyde, stained by 0.1% Crystal Violet.

RT-PCR:

Total RNA was isolated using Absolutely RNA Microprep Kit (Stratagene) according to the manufacturer's instructions from human samples. cDNA was synthesized using 0.2 ug of total RNA in 20 ul reaction mixture, containing oligo(dT)12-18 primers and Superscript II reverse transcriptase (Invitrogen), according to the manufacturer's instructions). To compensate for variable cDNA yields, the amount of cDNA for each PCR reaction was calibrated by using expression level of the housekeeping gene GADPH as a standard. Amounts of cDNA yielding equivalent amount of GADPH PCR product (at 20 cycles, data not shown) were used for subsequent PCR reactions. cDNAs were amplified using primers from Table 1 for human samples. All PCR reactions were run for 30 cycles (including those GADPH PCRs which are shown on pictures) and were performed in 20 μl under standard conditions using 1 U of Taq DNA Polymerase Recombinant (Invitrogen). The PCR products were analyzed on a 1.5% agarose gel containing ethidium bromide.

For each RNA sample, RT-PCR without reverse transcriptase was performed to confirm that no genomic DNA was isolated.

TABLE 1

Primers for RT-PCR (human samples)

| Gene | Forward primer | Reverse primer | Product size (bp) | Ta, (C.) |
|---|---|---|---|---|
| Oct-4 | CGACCATCTGCCGCTTTGAG (SEQ ID NO: 1) | CCCCCTGTCCCCCATTCCTA (SEQ ID NO: 2) | 573 | 61 |
| Nanog | AGCATCCGACTGTAAAGAATCTTCAC (SEQ ID NO: 3) | CGGCCAGTTGTTTTTCTGCCACCT (SEQ ID NO: 4) | 433 | 61 |
| GADPH | GAAGGTGAAGGTCGGAGTCA (SEQ ID NO: 5) | TTCACACCCATGACGAACAT (SEQ ID NO: 6) | 402 | 59 |
| Pax6 | AACAGACACAGCCCTCACAAAC (SEQ ID NO: 7) | CGGGAACTTGAACTGGAACTGAC (SEQ ID NO: 8) | 275 | 61 |
| AFP | CTTTGGGCTGCTCGCTATGA (SEQ ID NO: 9) | TGGCTTGGAAAGTTCGGGTC (SEQ ID NO: 10) | 175 | 59 |
| Brachyury | GAAGGTGGATCTCAGGTAGC (SEQ ID NO: 11) | CATCTCATTGGTGAGCTCCTT (SEQ ID NO: 12) | 251 | 59 |
| Sox1 | CTCACTTTCCTCCGCGTTGCTTCC (SEQ ID NO: 13) | TGCCCTGGTCTTTGTCCTTCATCC (SEQ ID NO: 14) | 849 | 61 |

Immunofluorescence:

For immunofluorescence embryonic cells were fixed in 96-well plate wells by 4% paraformaldehyde, permeabilized by 0.1% Triton-X and blocked by 10% bovine fetal serum (Invitrogen) in 0.1% Tween-20 (Sigma) PBS for 1 hour. Incubation with primary antibody was performed for 1.5 hours at room temperature. Primary antibody against following human antigens were used: Oct4 and Sox2 (both from R@DSystems). Incubation with secondary antibody (Alexa-488- and Alexa 546-labeled, Molecular probes) with DAPI (Molecular probes) was performed for 40 min. Between incubations specimens were washed with 0.1% Tween-20 in PBS three to five times, 10 minutes for each wash. Specimens were preserved in fluorescence mounting medium (Dako) and observed under fluorescent microscope (Leica).

Results for First Set of Experiments

A. Human Embryonic Stem Cells Cultured on Laminins-511 Proliferate and Remain Pluripotent in Chemically Defined Medium in Absence of Feeders On laminin-511, human embryonic stem cells were found to remain pluripotent in chemically defined medium for at least 105 days (20 passages).

Morphology:

Morphology of human embryonic stem cells cultured on Laminin-511 was very similar to that found for human embryonic stem cells cultured on Matrigel™ (Bendall, S., C., Stewart, M., H., Menendez, P., George, D., Vijayaragavan, K., Werbowetski-Ogilvie, T., Ramos-Mejia, V., Rouleau, A., Yang, J., Bossé, M., Lajoie, G. and Bhatia, M. (2007); IGF and FGF cooperatively establish the regulatory stem cell niche of pluripotent human cells in vitro. Nature, 2007 Aug. 30; 448(7157):1015-21.) or extracellular-matrix-coated plates (Klimanskaya, I., Chung, Y., Meisner, L., Johnson, J., West, M., D. and Lanza, R. (2005); Human embryonic stem cells derived without feeder cells. Lancet. 2005 May 7-13; 365(9471):1601-1603). See FIG. 1. But, unlike the two coatings mentioned above, recombinant human laminin-511 can be produced according to FDA requirements as a xeno-free, defined and nonimmunogenic compound and subsequently used in clinic.

Rt-PCR Markers:

Pluripotency markers Oct4 and Nanog were expressed at same extent by human embryonic stem cells cultured on laminins-551 in the chemically defined medium for 105 days, as pluripotent embryonic stem cells cultured on human fibroblast foreskin in the conventional medium. See FIG. 2.

Immunofluorescence:

Human embryonic stem cells expressed pluripotency markers like Oct4 and Sox2 at same extent as embryonic stem cells grown in conventional environment. See FIG. 3.

II. Methods for Second Set of Experiments

Human ES Cell Culture

Human ES cells of HS207, HS420 and HS401, originally derived in our laboratory at the Karolinska Institute were cultured on LN-511 coated laboratory dishes in (1) chemically defined O3 medium (a variant of mTeSR1 medium) and (2) chemically defined and xeno-free H3 medium (a variant of TeSR medium) at 37° C., 5% $CO_2$. Clinical grade ≥96% pure human albumin was purchased from Octapharma AB, Stockholm. Initially, cells of the lines were transferred on LN-511 in small pieces from feeder cell layer by careful scratching using a sterile knife. Cells were fed once a day with fresh medium pre-warmed in an incubator for 1 hour, except for the first day after a passage when only a few drops of fresh medium were added. Cells were routinely passed once in 6-7 days by exposure to TrypLE™ Express (GIBCO Invitrogen Corporation, Paisley, Scotland) for 1.5 minutes at room temperature. Then they were washed two times on the dish with the medium, gently scraped, pipetted to break into small pieces (not a single cell suspension) and plated in 1:2 or 1:3 ratio (up to 1:6 ratio if a large number of cells was needed). Control cells of the same line were cultured on Matrigel in O3 medium and on human foreskin fibroblasts. Laboratory dishes were coated. Prior to use, dishes were pre-warmed in an incubator for 1 hour and then carefully washed twice with the pre-warmed medium.

Preparation of O3 Medium (a Variant of mTeSR1)

Stock A was prepared by adding 165 mg of thiamine and 50 mg of reduced glutathione to 500 ml of distilled water as described in Ludwig, Nat. Methods 3:637-646 (2006), but without L-ascorbic acid. The distilled water was purchased from GIBCO Invitrogen Corporation. Then the solution was filtered (0.22 µm filter), aliquoted and frozen at −20° C.

Stock B was prepared as described in Ludwig, but without selenium, insulin and holo-transferrin. Then 6 µg of Phenol Red was added, carefully stirred and filtered. Stock B could be stored at +4° C. up to 2 months.

Stocks of transforming growth factor (TGF)-β1, pipecolic acid, γ-aminobutyric acid (GABA) and LiCl were prepared and stored as described in Ludwig.

To prepare 100 ml of O3 medium D-MEM/F12 medium was supplemented with 20 ml of Stock B, 200 µl of TGF-β1 stock, 13 µl of pipecolic acid stock, 200 µl of GABA stock, 200 µl of LiCl stock, 1 ml of MEM non-essential amino acid solution (GIBCO Invitrogen Corporation), 1 ml of 200 mM L-glutamine solution (GIBCO Invitrogen Corporation) and 2 ml of insulin-transferrin-selenium supplement (GIBCO Invitrogen Corporation). To compensate the salt balance and to adjust pH of the medium 145 mg of NaCl and 56 mg of $NaHCO_3$ were added. Then the solution was thoroughly mixed, and the pH of the medium at room temperature was adjusted to 7.4 using 10 N NaOH. The solution was filtered using a 0.22 µm filter, then 200 µl of chemically defined lipid concentrate (GIBCO Invitrogen Corporation) was added.

O3 medium could be stored at +4° C. up to 1 month. Before use the medium was supplemented with 96 ng/ml of recombinant human FGF basic (R@D Systems Europe LTD, Abingdon, England) and 40 µg/ml of ascorbic acid (SigmaAldrich).

Preparation of H3 Medium (a Variant of TeSR1).

Stock A was prepared as described above for O3 medium.

Human albumin solution (Albuminativ) was purchased from Octapharma AB, Stockholm, Sweden. The solution was dialyzed 3 times against cell culture phosphate-buffered saline (PBS) for 3 hours each time using a 12-14 Kda dialysis membrane (Spectrum Laboratories, Inc., Rancho Dominguez, Calif.) and subsequently once against D-MEM/F12 medium. Using measurement of optical density the final concentration of the protein in the solution was assessed. In this case stock B was mixed using appropriate volume (depended on the concentration) of the dialyzed human albumin solution to achieve the same concentration of albumin as in case of Stock B for O3 medium (described above). Trace elements and phenol red was added, D-MEM/F12 instead of water was used.

Stock of TGF-β1 was prepared as described in Ludwig, but dialyzed human albumin instead of bovine albumin was used. All other stocks were prepared as described above.

H3 medium was mixed was described for O3, but NaCl was not added at all.

Before use the medium was supplemented with 96 ng/ml of carrier free recombinant human FGF basic (R@D Systems Europe LTD, Abingdon, England) and 40 µg/ml of ascorbic acid (SigmaAldrich).

Laminins and Other Coating Materials

Figure 14:
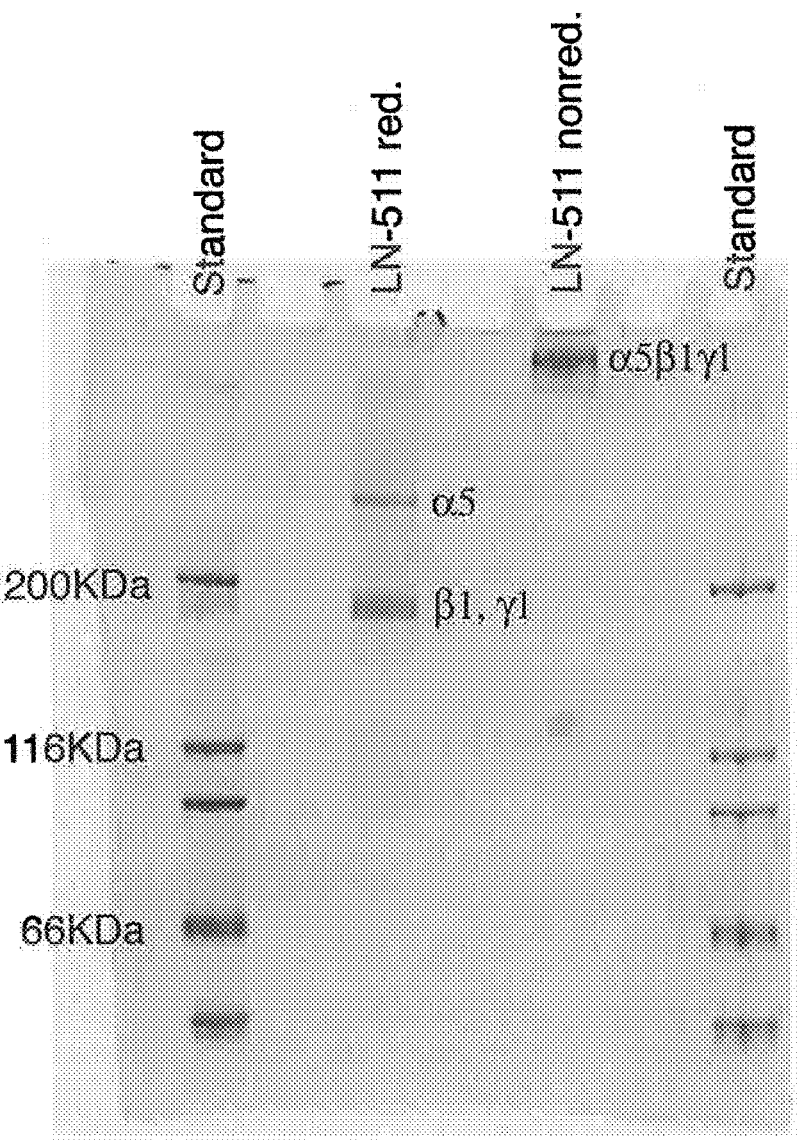
FIG. 14 shows the characterization of human recombinant LN-511 used in the article using 3-8% gradient SDS-PAGE under reducing and non-reducing conditions. The protein was visualized using Sypro Ruby protein staining.

Human recombinant LN-511, available from BioLamina, AB, Stockholm, was produced in human embryonic kidney cells (HEK293; ATCC CRL-1573) sequentially transfected with full-length laminin γ1, β1 and α5 constructs. For protein production, the HEK293 cells were cultured in Dulbecco's modified Eagle's medium (DMEM) supplemented with GlutaMax I and 4.5 g/l glucose (GIBCO Invitrogen Corporation) for up to six days. The LN-511 molecules were affinity-purified using anti-FLAG matrix (Sigma), and then characterized using 3-8% (FIG. 14) and 4-15% gradient SDS-PAGE under reducing and nonreducing conditions. The proteins were visualized using Sypro Ruby (Bio-Rad) protein staining and immunostaining of the chains on polyvinylidene difluoride membranes. To further characterize the protein, Western blot analysis with antibodies against the laminin α5, β1, and γ1 chains was performed. The preparations contained all three chains of the right size. Human recombinant Laminin-411 was produced in a similar fashion as LN-511. All other ECM proteins were obtained as described previously.

Cell Contact Area Measurement

MaxiSorp 96-well plates (Sarstedt, Numbrecht, Germany) were coated with ECM proteins as previously described and blocked by 1% heat-denatured BSA solution. Undifferentiated ES cells were split into single-cell suspension, filtered through 40 µm sterile cell sieve and plated at cell density of 700 cells/$mm^2$ upon ECM-coated plates and were left to adhere for one hour at 37° C. Non-adherent cells were washed away, and adherent cells were fixed for 20 minutes by 5% glutaraldehyde, washed and stained by 0.1% Crystal Violet. Photos of 6-10 random fields were taken, and the cell contact area of 13-93 cells was measured using the Volocity imaging software (Improvision, Waltham, Mass., http://www.improvision.com). To measure the cell area of nonspread human ES cells, the cells were plated on poly-D-lysine for 20 minutes, fixed and stained as described above.

Adhesion-Blocking Assay Using Anti-Integrin Antibody

Adhesion-blocking assays were performed. Briefly, plates were coated by LN-511 and blocked by 1% heat-denatured BSA solution. ES single-cell suspension was incubated with function-blocking anti-integrin antibodies (concentration as recommended by supplier) for 30 minutes, plated on LN-511-coated plates and allowed to adhere for 1 hour at 37° C. Non-attached cells were removed, the remaining cells were fixed, and adherent cells were fixed for 20 minutes by 5% glutaraldehyde, washed and stained by 0.1% Crystal Violet. After one hour, Crystal Violet was extracted from cells by 10% acetic acid and quantified by measuring optical density at 570 nm.

Cell Adhesion to Surface Coated by Anti-Integrin Antibody Assay

The assay was designed to identify integrin receptors that are expressed in sufficient amounts to retain cells attached to the surface coated with anti-integrin-specific antibody. Max-iSorp 96-well plates (Nunc) were coated with purified anti-integrin antibodies at a concentration of 10 µg/ml at +4° C. overnight and later washed and blocked with 1% BSA solution. ES cells were plated on antibody-coated plates and allowed to adhere for 1 hour at 37° C. Nonattached cells were removed, and the remaining cells were fixed, stained, and quantified as described above. Error bars show SEM.

RT-PCR

Total RNA was isolated using Absolutely RNA Microprep Kit (Stratagene, La Jolla Calif., www.stratagene.com) according to the manufacturer's instructions. cDNA was synthesized using 0.2 µg of total RNA in 20 µl reaction mixture, containing oligo(dT)12-18 primers and Superscript II reverse transcriptase (GIBCO Invitrogen Corporation), according to the manufacturer's instructions. To compensate for variable cDNA yields, the amount of cDNA for each PCR reaction was calibrated by using expression level of the housekeeping gene for glyceraldehyde-3-phosphate dehydrogenase (GAPDH) as a standard. Amounts of cDNA yielding equivalent amount of GAPDH PCR product (at 20 cycles, data not shown) were used for subsequent PCR reactions. To analyze expression of different markers of pluripotency or differentiation of hES cells cDNAs were amplified using primers described in Table 2. To analyze expression of different laminin chains, primers were used. All PCR reactions were run for 30 cycles (including those GAPDH PCRs which are shown in the figures) and were performed in 20 µl under standard conditions using 1 U of Taq DNA Polymerase Recombinant (GIBCO Invitrogen Corporation). The PCR products were analyzed on a 1.5% agarose gel containing ethidium bromide. For each RNA sample, RT-PCR without reverse transcriptase was performed to confirm that no genomic DNA was isolated.

TABLE 2

Primers for RT-PCR (human samples)

| Gene | Forward primer | Reverse primer | Product size (bp) | Ta, (C.) |
|---|---|---|---|---|
| Oct-4 | CGACCATCTGCCGCTTTGAG (SEQ ID NO: 1) | CCCCCTGTCCCCCATTCCTA (SEQ ID NO: 2) | 573 | 61 |
| Nanog | AGCATCCGACTGTAAAGAATCTTCAC (SEQ ID NO: 3) | CGGCCAGTTGTTTTTCTGCCACCT (SEQ ID NO: 4) | 433 | 61 |
| GADPH | GAAGGTGAAGGTCGGAGTCA (SEQ ID NO: 5) | TTCACACCCATGACGAACAT (SEQ ID NO: 6) | 402 | 59 |
| Pax6 | AACAGACACAGCCCTCACAAAC (SEQ ID NO: 7) | CGGGAACTTGAACTGGAACTGAC (SEQ ID NO: 8) | 275 | 61 |
| α-feto protein (AFP) | CTTTGGGCTGCTCGCTATGA (SEQ ID NO: 9) | TGGCTTGGAAAGTTCGGGTC (SEQ ID NO: 10) | 175 | 59 |
| Brachyury | GAAGGTGGATCTCAGGTAGC (SEQ ID NO: 11) | CATCTCATTGGTGAGCTCCTT (SEQ ID NO: 12) | 251 | 59 |
| Sox1 | CTCACTTTCCTCCGCGTTGCTTCC (SEQ ID NO: 13) | TGCCCTGGTCTTTGTCCTTCATCC (SEQ ID NO: 14) | 849 | 61 |

Immunofluorescence

For immunofluorescence studies, ES cells were cultured and fixed in 8-well slide chambers (BD Biosciences) or 96-well plate wells by 4% paraformaldehyde, permeabilized by 0.1% Triton-X and blocked by 10% bovine fetal serum (GIBCO Invitrogen Corporation) in phosphate-saline buffer (PBS) containing 0.1% Tween-20 (Sigma-Aldrich, St. Louis, Mo.) for one hour. Incubation with primary antibody was performed for 1.5 hours at room temperature. Incubation with secondary antibody and 4,6-diamidino-2-phenylindole (DAPI, Molecular Probes) was performed for 40 minutes. Between incubations, specimens were washed with 0.1% Tween-20 in PBS buffer three to five times. Specimen were preserved in fluorescence mounting medium (Dako, Glostrup, Denmark), and observed under a fluorescence microscope (Leica, Heerbrugg, Switzerland).

Real-Time PCR Quantification of Different mRNAs

Total RNA was isolated and cDNA was synthesized as described above for RT-PCR. Real-time quantitative RT-PCR Taqman assays were performed using the Applied Biosystems 7300 Real-Time PCR System (Applied Biosystems, Foster City, Calif.). All reactions were done in quadruplicates with the use of pre-developed gene expression assay mix (Applied Biosystems) containing primers and a probe for the mRNA of interest. Additional reactions for each experiment included pre-developed gene expression assay mix for GAPDH for normalizing the RNA input. All data was analyzed with 7300 System SDS Software v 1.4.

Western Blot and Densitometry Analysis

After culturing on LN-511, hES cells were collected, counted and pelleted by centrifugation, mixed with non-reduced SDS-PAGE sample buffer to equal concentration of 2000 cells/µl and sonicated 5 times for 15 seconds. Gradient 4-12% gels were used for SDS electrophoresis and the proteins were transferred to PVDF membranes. Membranes were blocked by 5% milk solution in PBS-0.1% Tween buffer for 2 hours. Primary antibody against Oct4 and Sox2 (both from Millipore) in 5% milk solution in PBS with 0.1% Tween buffer were incubated with the membranes overnight at +4° C. After being washed 4 times, HRP-conjugated secondary antibodies 5% milk solution in PBS with 0.1% Tween buffer (dilution 1:1000) were incubated with the membranes for 40 minutes at room temperature and washed 5 times with PBS. Chemoluminescent HRP-substrate from Amersham Biosciences was used for visualization. Films were scanned at 2,400 dpi and analyzed by the ChemiImager5500 program (1 D-Multi Line densitometry mode). Human ES cells cultured on Matrigel and on feeder cells were used as positive control.

FACS Analysis

Cells were removed from the culture dish with Trypsin/EDTA, dissociated into a single cell suspension and resuspended in ice-cold FACS buffer (2% fetal bovine serum, 0.1% sodium azide in Hanks buffer). Incubation with primary antibodies against SSEA-4, SSEA-1 (both from R&D Systems, Minneapolis, Minn. USA), Tra1-60 or Tra1-81 (both from Millipore, Billerica, Mass.) was performed for one hour on ice. Then cells were washed 3 times with ice-cold FACS buffer. After that, cells were probed in FACS buffer with 1:400 dilution of Alexa Fluor anti-mouse secondary antibodies (GIBCO Invitrogen Corporation) for 30 minutes in the dark and washed 4 times. Control cells were incubated with mouse immunoglobulins and, subsequently, with the secondary antibody as described above. Cells were analyzed on FACSCalibur Flow Cytometer (Becton Dickinson, San Jose, Calif.). Data were analyzed with CellQuest software (Becton Dickinson). Analysis of Oct4 expression was also performed.

Karyotyping

Karyotyping of the cell lines was carried out using standard Q-banding techniques at passage 20 on LN-511. Samples of cells were treated with colcemid KaryoMAX (0.1 µg/ml, Gibco Invitrogen Corporation) for up to 4 hours, followed by dissociation with TrypLE™ Express (Gibco Invitrogen Corporation). The cells were pelleted via centrifugation and re-suspended in pre-warmed 0.0375 M KCl hypotonic solution and incubated for 10 minutes. Following centrifugation, the cells were resuspended in fixative (3:1 methanol:acetic acid). Metaphase spreads were prepared on glass microscope slides and G-banded by brief exposure to trypsin and stained with 4:1 Gurr's/Leishmann's stain (Sigma-Aldrich Co.). A minimum of 10 metaphase spreads were analyzed and an additional 20 were counted.

Teratoma Formation

Teratoma formation experiments were done by implantation of approximately 106 cells beneath the testicular capsule of a young (7 weeks old) severe combined immunodeficiency (SCID) mouse. Three animals per each cell line were used. Teratoma growth was determined by palpation every week, and the mice were sacrificed 8 weeks after the implantation. The teratomas were fixed, and sections were stained with hematoxylin and eosin (HE) or with hematoxylin, eosin and PAS (HE-PAS). The presence of tissue components of all three embryonic germ line layers was shown, as analyzed from the stained sections. All animal experiments were performed at the infection-free animal facility of the Karolinska University Hospital in accordance with ethical committee approval.

Embryoid Body Formation

ES cells were dissociated from LN-511 coated cell culture dishes as described above for passaging them, broken into pieces and cultured in suspension 96-well plates (Sarstedt). The medium used for this was Knockout DMEM (GIBCO Invitrogen Corporation) supplemented with 2 mM L-glutamine, 20% fetal calf serum (GIBCO Invitrogen Corporation), 0.1 mM β-mercaptoethanol (GIBCO Invitrogen Corporation) and 1% non-essential amino acids (GIBCO Invitrogen Corporation). After 1 week in suspension, the embryoid bodies were transferred into gelatin coated tissue cell culture 96-well plates (Sarstedt), cultured for 1 week, then fixed, stained with antibodies against markers of all three embryonic germ line layers (smooth muscle actin, Nestin, MAP-2 and α-fetoprotein, all three antibodies were from Millipore) and analyzed as described above for immunofluorescence.

Statistics

Statistical significance was determined by the Student's two-tailed t-test for unequal variances.

Results for Second Set of Experiments

Figure 4A:
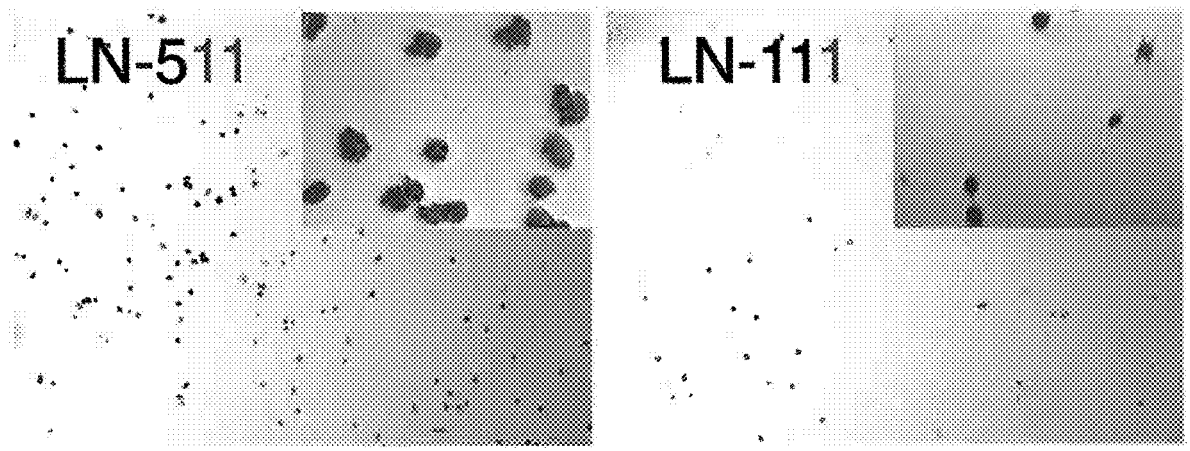
FIG. 4a shows Crystal Violet staining of human ES cells adherent to LN-511 and LN-111. Magnification: ×5 (insets: ×20)
Figure 4B:
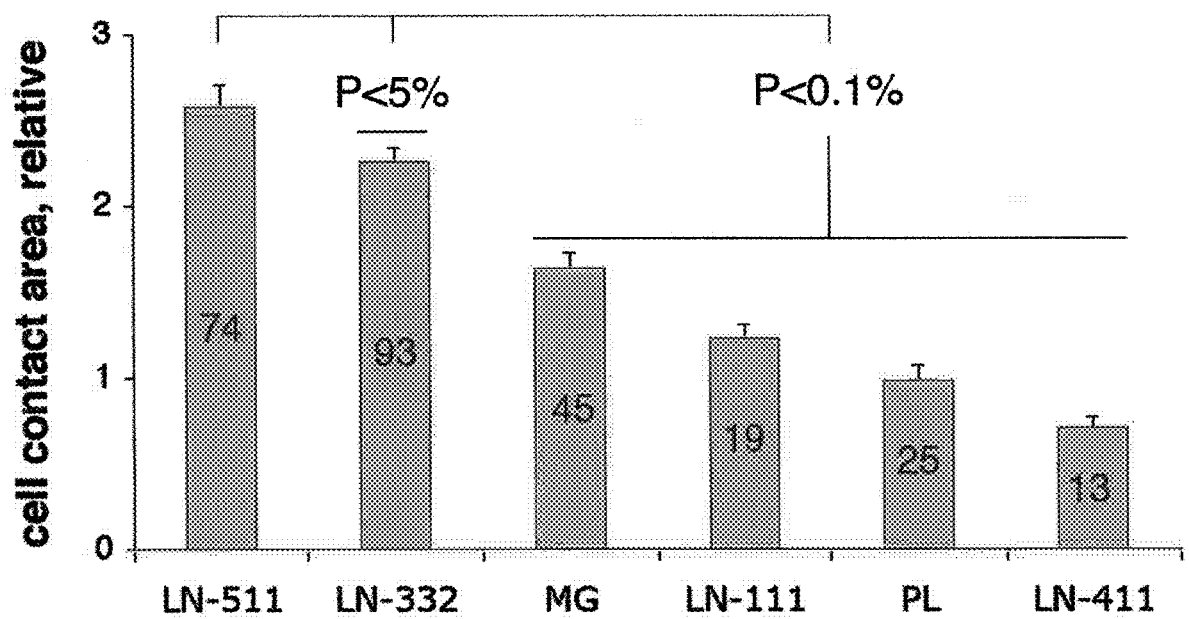
FIG. 4b is a graph showing the contact area of ES cells to different adhesive substrata. Values are shown as average relative contact area (compared with the cells plated on poly-D-lysine). Statistical significance (P) was calculated by the Student t-test. Error bars show standard error (SE); number inside each bar shows number of independent measurements. Abbreviations: LN, laminins; MG, Matrigel; PL, poly-D-lysine.

A. Strong Adhesion to LN-511 Results in a Large Contact Area of the Human ES Cell with the Substratum It is known that proliferation of cells is strongly dependent on the cell contact area with their adhesive substratum. This notion agrees with our previous findings concerning adhesion of mouse ES cells to and their proliferation on different laminins and other ECM proteins. To compare adhesion properties of human ES cells to different ECM proteins, Applicants performed human ES cell adhesion assays on LN-511, LN-332, LN-411, LN-111, Matrigel or poly-D-lysine substrata (FIGS. 4a and 4b). The average contact area of an adherent human ES cell grown on LN-511 was about 1.6 times higher than that of cells plated on Matrigel and about 1.2 times higher than that of cells plated on LN-332 (FIG. 4b). Embryonic stem cells spreading on other coatings tested were significantly less than that on LN-511.

B. HS207, HS420 and HS401 Cells Express LN-511

Figure 4C:
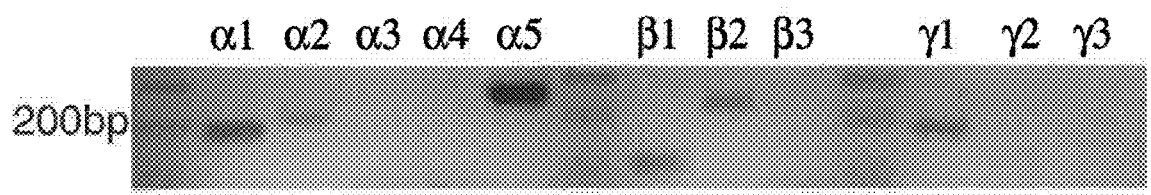
FIG. 4c shows the RT-PCR analysis of total RNA isolated from HS420 cells. Primer sets for all known laminin chains were used.

It has been reported that cells of several human ES cell lines express laminin α5, β1 and γ1 chains. To find out if it is a unique property of those lines, Applicants performed RT-PCR on cDNA originated from cells of HS207, HS420 and HS401, using primers specific for different laminin chains. All three transcripts for α5, β1 and γ1 laminin chains along with α1, α2 and β2 were easily detectable, demonstrating that LN-511 was expressed in hESC cells of all three lines (FIG. 4c). Interestingly, consistent with previous reports transcription of α3 and β3 laminin chains were not registered, suggesting that LN-332 was not produced in the embryonic cells.

Figure 5A:
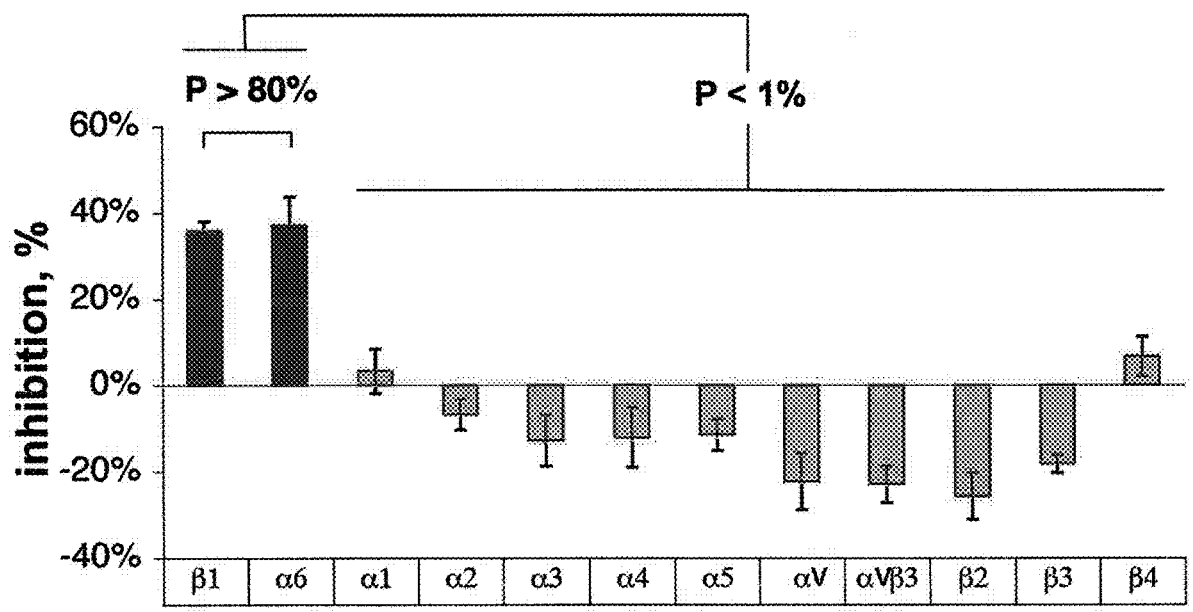
FIG. 5a is a graph showing the inhibition of human ES cell adhesion to LN-511 by different anti-integrin antibodies. Bars represent (from left to right) β1, α6, α1, α2, α3, α4, α5, αV, αVβ3, β2, β3, β4 (all from Millipore). IgG were used as a control for uninhibited cell adhesion. Error bars show standard error (n=4). Statistical significance (P) was calculated by the Student t-test.

C. Contact with LN-511 Depends on Integrin α6β1 which is Highly Expressed in Human ES Cells In order to identify integrin receptors potentially involved in hES binding to LN-511, Applicants performed an adhesion-blocking assay. Single cell suspension of embryonic cells was incubated on LN-511 coated dishes in media with function-blocking antibodies against various integrin receptors. Of all integrin subunits tested, β6 and β1 were the most important ones involved in interaction with LN-511 under those conditions (FIG. 5a). Since single cell suspension is not a favorable state for human ES cells, the experiment was repeated three times giving the same result (data not shown).

Figure 5B:
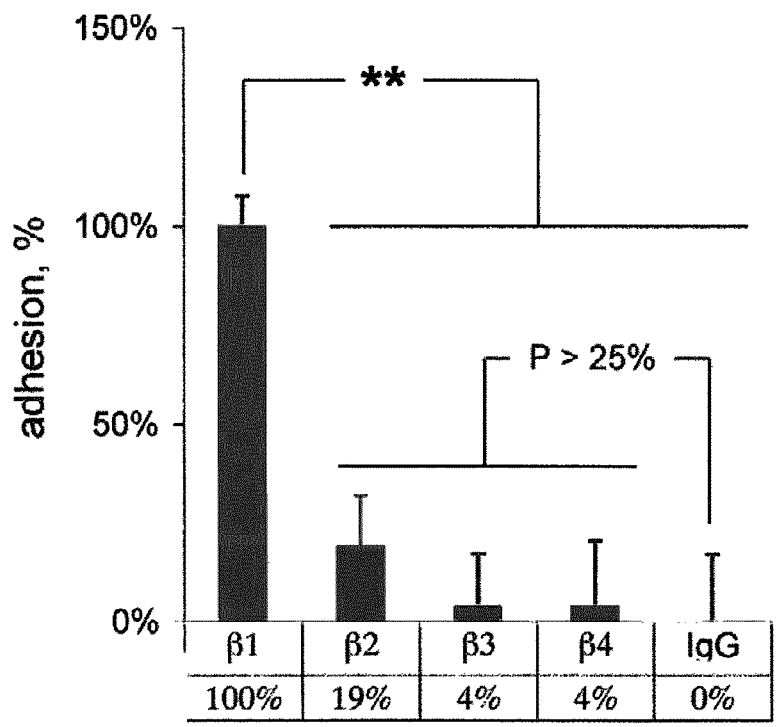
FIG. 5b is another graph showing adhesion of hES cells to surface coated by different anti-integrin antibodies. Bars represent (from left to right) adhesion to β1 (100%), β2, β3, β4 and IgG. Error bars show standard error (n=4). Statistical significance (P) calculated by the Student t-test is shown: **, P<0.01.

Recently it has been shown that α6β1 is the most abundant integrin isoform on the hES cell surface. To further address the question of integrin subunit amounts on hES cell surfaces, Applicants immobilized anti-integrin antibodies on plastic surface and identified antibodies that could bind and retain hES cells attached. Applicants found out that antibodies against β1 integrin subunit provided strongest adhesion, while antibodies against β2, β3, and β4 retained the cells much worse attached to the surface (19%, 4% and 4% respectively, in comparison with adhesion to antibodies against β1) (FIG. 5b).

Figure 5C:
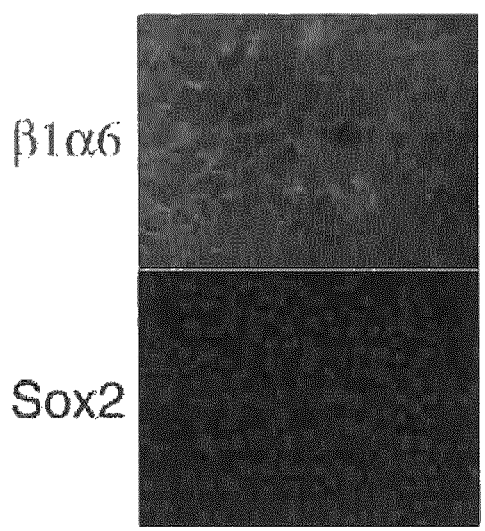
FIG. 5c is a set of immunofluorescence pictures showing integrin α6 co-expression with β1 integrin subunit in pluripotent (Sox2-positive) hES cells cultured on LN-511. Magnification ×40.

Immunofluorescence staining confirmed expression of α6 and β1 integrin subunits in undifferentiated (Sox2 positive) hES cells and co-localization of them on the surfaces of the cells (FIG. 5c).

Figure 6A:
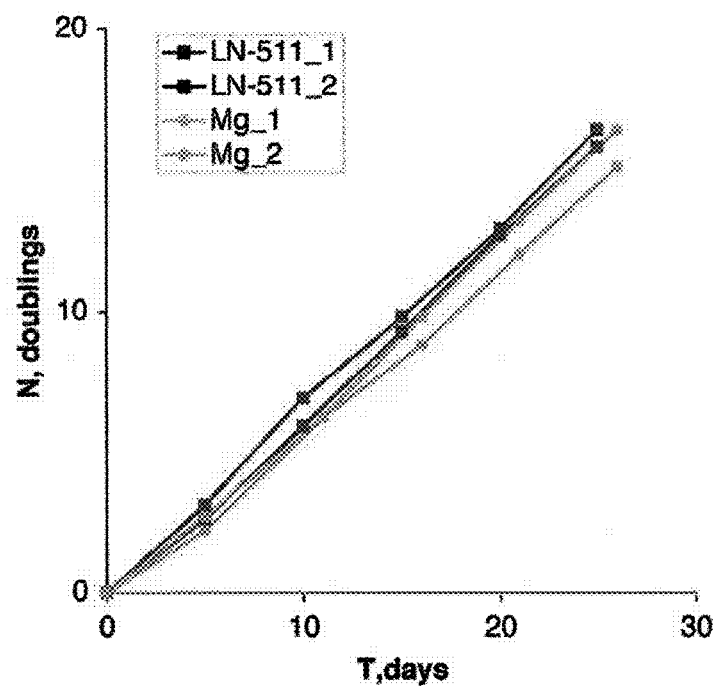
FIG. 6a shows growth curves for hES cells cultured in O3 medium on LN-511 and Matrigel. The cells were passaged as described below for the long-term experiment. After each TrypLE™ Express treatment and subsequent washing only one third of the cells in clumps was used to plate on fresh LN-511 or Matrigel coated dishes. The rest was dissociated into single cell suspension and counted. The experiment was performed in two independent duplicates for each coating. After the fifth passage, a part of the cells was fixed and analyzed by immunofluorescence staining confirming that majority of the cells still expressed marker of pluripotency Nanog.
Figure 6B:
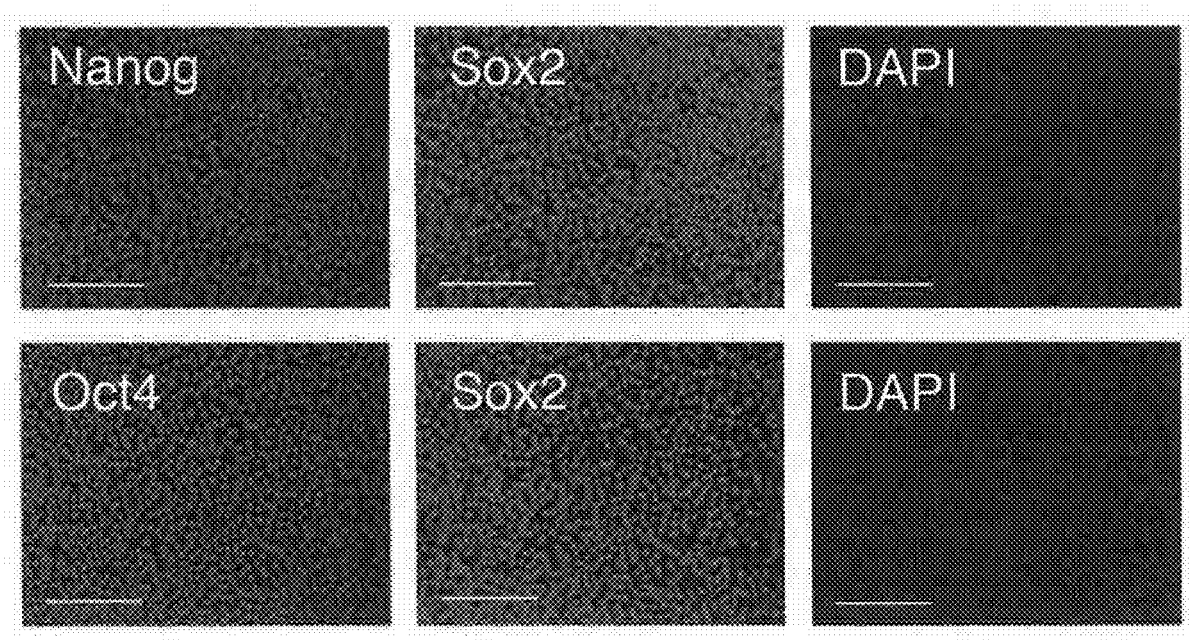
FIG. 6b shows immunostaining of HS207 cells with anti-Nanog (labeled as Nanog), anti-Sox2 (Sox2) and anti-Oct4 (Oct4) antibodies after 20 passages (6 months) on LN-511 in O3 medium. Right panels are nuclear DAPI staining. Same staining represented with higher magnification. Magnification: ×20. Bars: 0.15 mm.
Figure 6C:
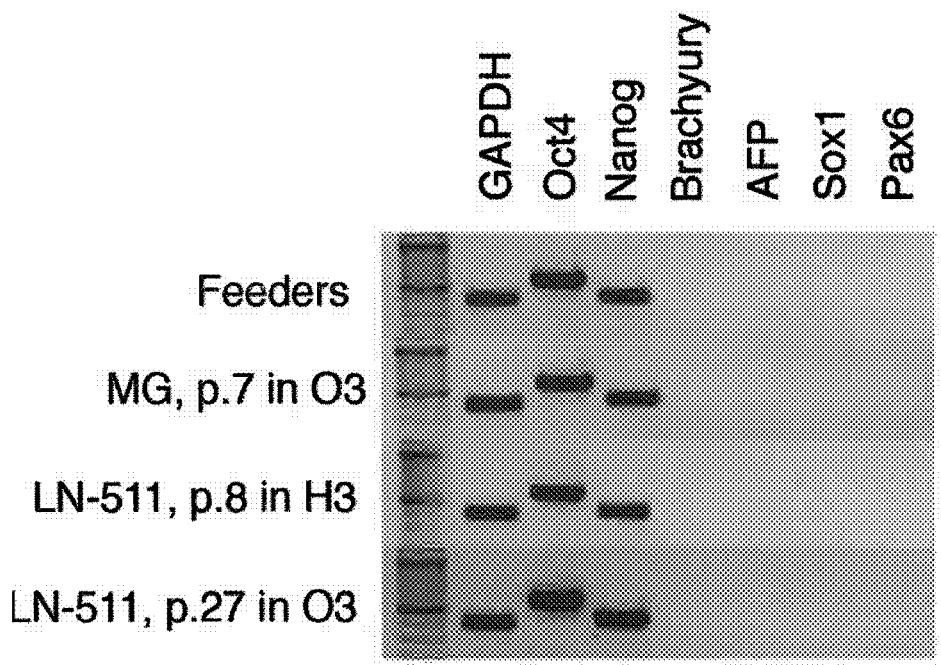
FIG. 6c shows RT-PCR analysis of total RNA isolated from H207 cells grown on feeder cells (depicted as Feeders), on Matrigel after 7 passages in O3 medium (MG, p7 in O3), on LN-511 after 8 passages in H3 medium (LN-511, p.8 in H3) and on LN-511 after 27 passages in O3 medium (LN-511, p.27 in O3). Primer sets for pluripotency markers Oct4 and Nanog; differentiation markers Brachyury, α-fetoprotein, Sox1, and Pax6; and a housekeeping gene for glyceraldehyde-3-phosphate dehydrogenase (GAPDH) were analyzed.
Figure 9:
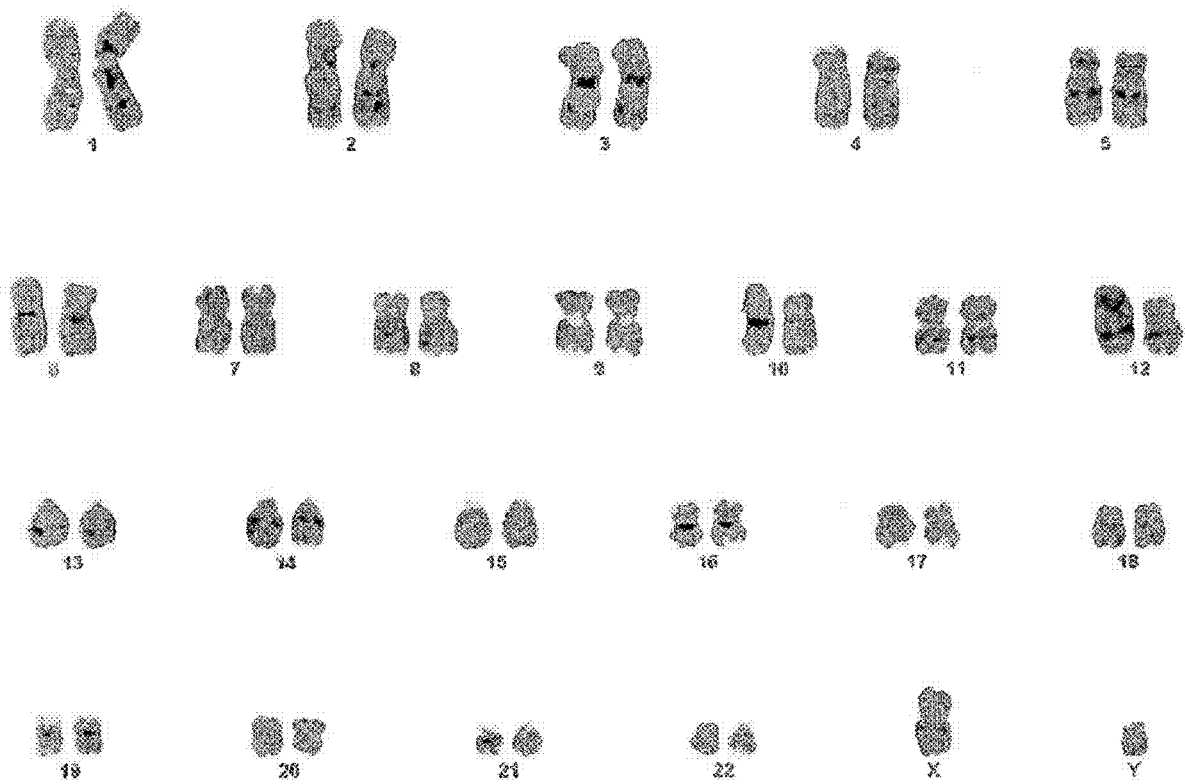
FIG. 9 shows G-banding chromosome analysis of HS207 cells after 20 passages on LN-511.

D. Human ES Cells Self-Renew on Human Recombinant LN-511 in Chemically Defined Xeno-Free Medium for at Least 4 Months To study the ability of LN-511 to support self-renewal, Applicants cultured the three hES cell lines in O3 and H3 media. The HS207, HS420 and HS401 cell lines proliferated robustly in both media. Normally, the cells were passaged in small clumps every 6-7 days in 1:2 or 1:3 ratios, but they could be passed in a 1:6 ratio if a large number of cells was needed. The cells exhibited similar proliferation rate and phenotypes in both media. As shown in FIG. 6a, human ES cells on LN-511 proliferated at a stable rate at least as high as that of the cells grown on Matrigel. At the time of writing, the HS420, HS207 and HS401 lines had undergone 28, 27 and 25 passages in O3 medium, respectively (5-6 months in culture). Karyotypes were normal for all three lines after 20 passages (FIG. 9). The HS420 and HS207 lines have, thus far, proliferated for 29 and 27 passages in H3, respectively (5 months). Immunofluorescence and RT-PCR analyses revealed that hES cells maintained high expression level of pluripotency markers, such as Oct4, Nanog, and Sox2 (FIGS. 6b and 6c).

When passaging the hES cells, they were plated in small clumps, not as single cell suspension. Interestingly, already on the following day the cells spread over the surface as a monolayer (appeared as very thin disks) suggesting that the affinity to the LN-511 coated surface was comparable or even higher than the adhesion between cells. Usually, when plated on 96-well culture plates, the cells first formed a thin confluent layer, after which they started to form cell layers by growing on top of cells. There was a difference between the monolayer on LN-511 and cells growing on feeders or Matrigel, where the cells appeared as less homogeneous and in thicker colonies.

Figure 6D:
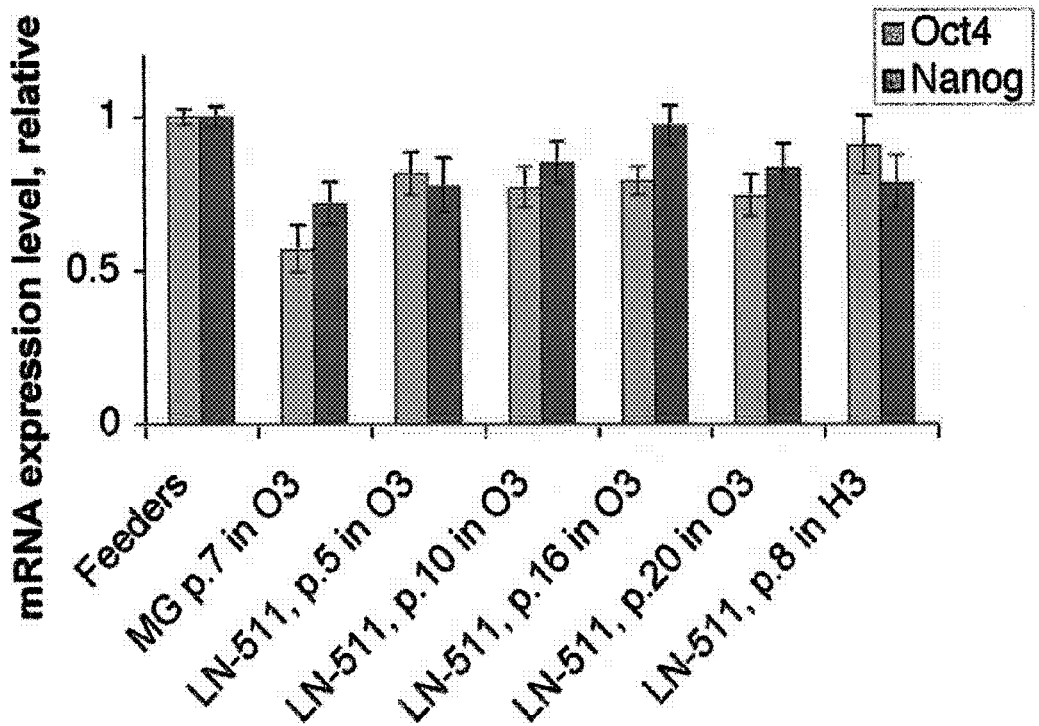
In FIG. 6d, real-time quantitative RT-PCR analysis was used to compare number of mRNA transcripts of pluripotency markers Oct4 (grey bars) and Nanog (black bars) at different timepoints of the experiments in HS207 cells cultured on LN-511 and on Matrigel with that of HS207 cells cultured on feeder cells. Bars represent (from left to right) levels of Oct4 and Nanog expression in control HS207 cells cultured on feeder layer (Feeders) taken as standard values to compare, in HS207 cells cultured on Matrigel after 7 passages in O3 medium (MG, p.7 in O3), in H5207 cells cultured on LN-511 after 5 (LN-511, p.5 in 03), 10 (LN-511, p.10 in O3), 16 (LN-511, p.16 in O3), 20 (LN-511, p.20 in O3) passages in O3 and in the cells on LN-511 after 8 passages in H3 (LN-511, p.8 in H3). Error bars show 95% confidence interval.
Figure 6E:
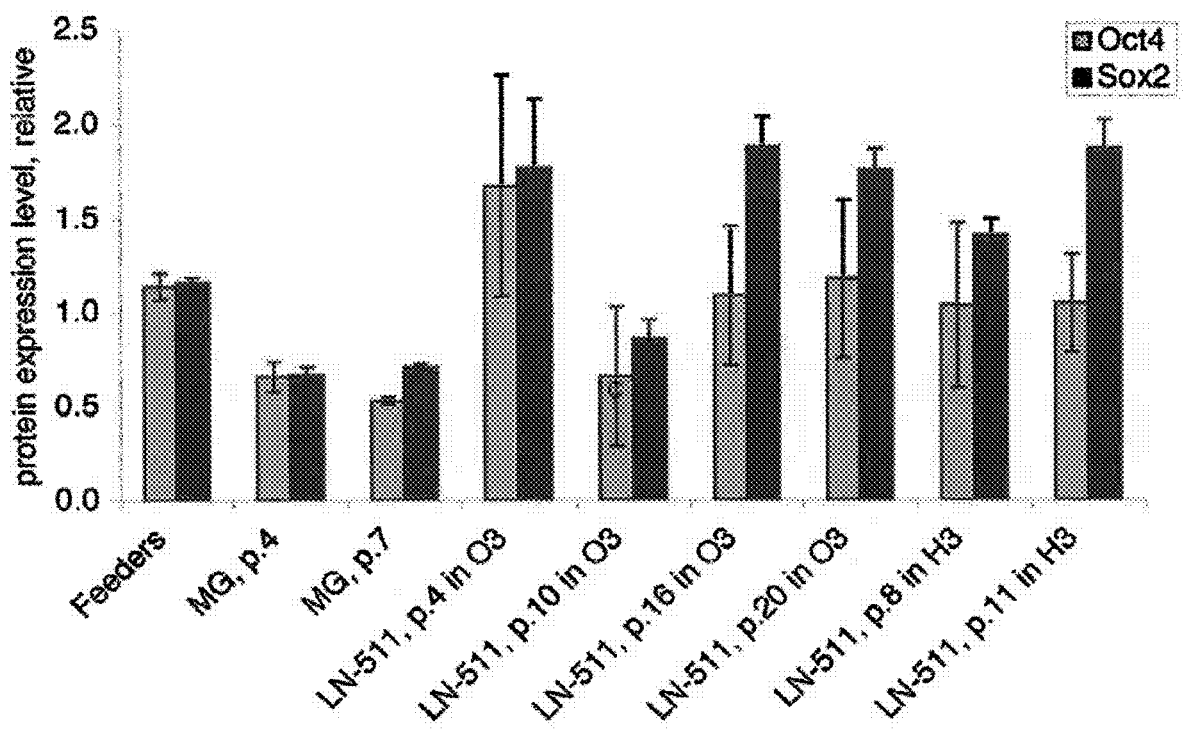
FIG. 6e shows expression of pluripotency markers Oct4 and Sox2 in HS207 cells cultured on feeder cells, Matrigel and LN-511 at different time points and in different media as measured by Western blot and quantified by densitometry. Grey bars represent expression levels of Oct4, black ones—Sox2. Abbreviations are similar to FIG. 6d. Error bars represent range.
Figure 10:
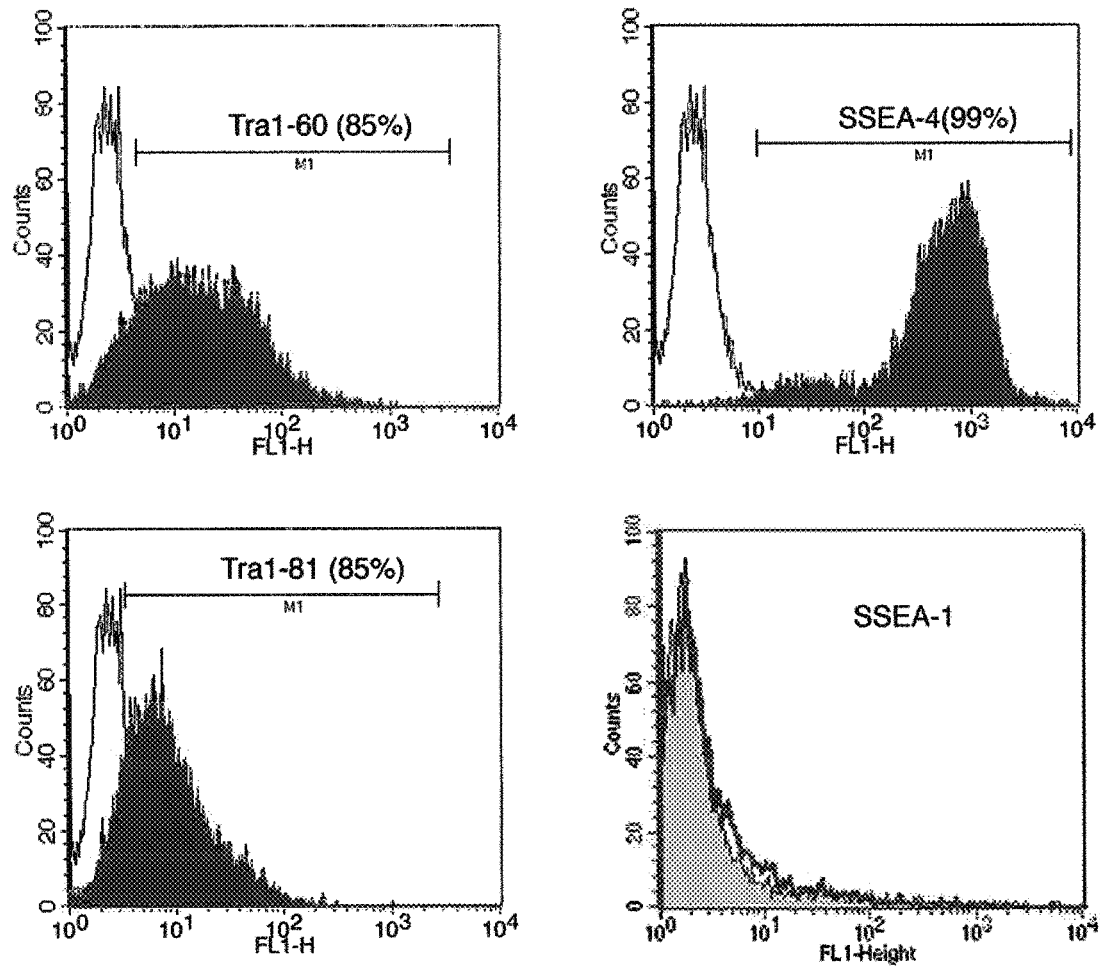
FIG. 10 shows FACS analysis of HS207 cells after 20 passages on LN-511 in O3 medium for cell surface markers of pluripotency (SSEA-4, Tra1-60, Tra1-81) and for cell surface marker of differentiation SSEA-1. The percentages of SSEA-4, Tra1-60, and Tra1-81 positive cells are listed in parentheses.
Figure 11:
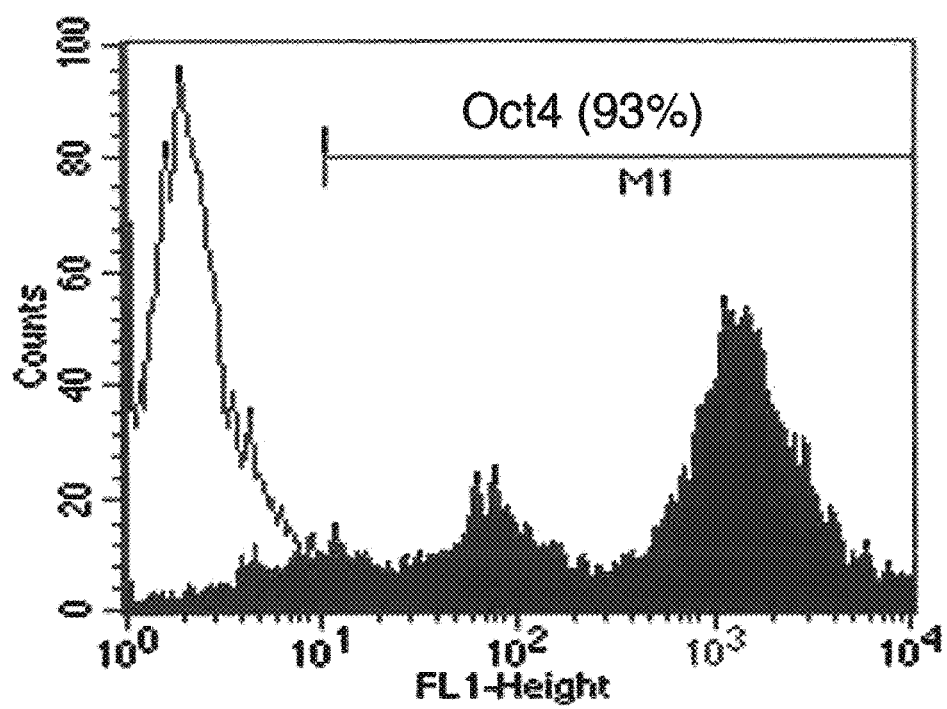
FIG. 11 shows FACS analysis of HS207 cells after 10 passages on Matrigel in O3 medium for markers of pluripotency Oct-4 and SSEA-4. The percentage of positive cells is listed in parentheses.
Figure 11:
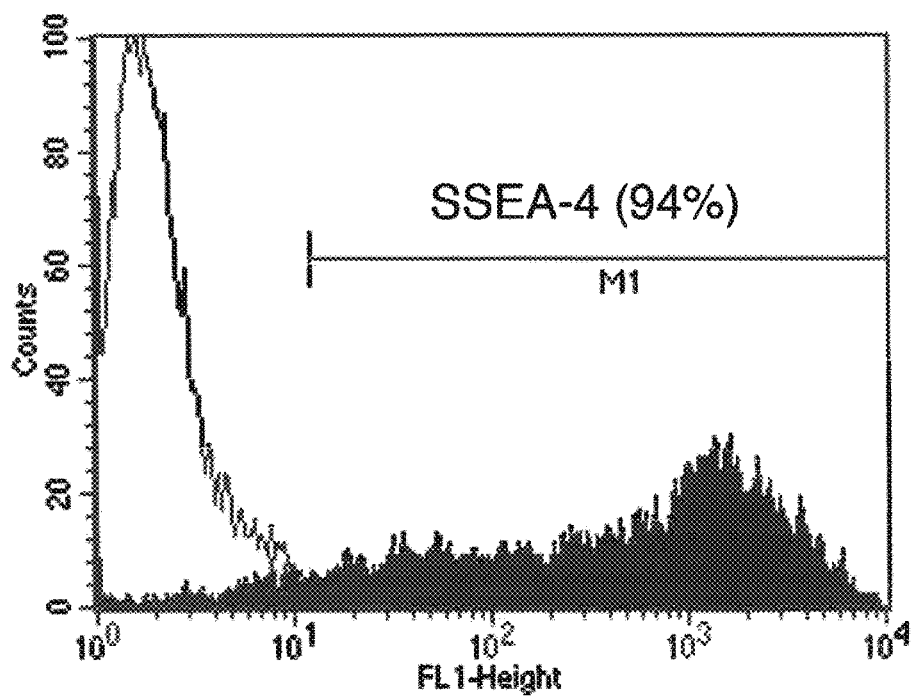

Even qualitatively Oct4 and Sox2 positive cells with stable proliferation rate can lose pluripotency. To quantify the expression of specific pluripotency markers, Applicants collected samples of hES cells cultured on LN-511 at different time points, and using real-time quantitative RT-PCR and quantitative Western blot analysis compared the expression levels of the main pluripotency markers with that of cells plated on Matrigel or on a layer of feeder cells (FIGS. 6d and 6e). Real-time quantitative RT-PCR revealed that the levels of Oct4 and Nanog expression of hES cells cultured in both media did not decline with time and were stably higher than that of cells plated on Matrigel and comparable with the expression levels of cells plated on feeder cells. Quantification of Western blots revealed similar results for Oct4 and Sox2. Analysis of the cells cultured on LN-511 by fluorescent-activated cell sorting (FACS) demonstrated that majority of the cells expressed markers of pluripotency Oct-4, SSEA-4, TRA1-60, and TRA1-81, and, simultaneously, expressed only minor amount of SSEA-1 (FIG. 6f; FIG. 10). Similar analysis of human ES cells cultured on Matrigel revealed slightly less number of Oct-4 and SSEA-4 positive cells (FIG. 11).

Figure 12:
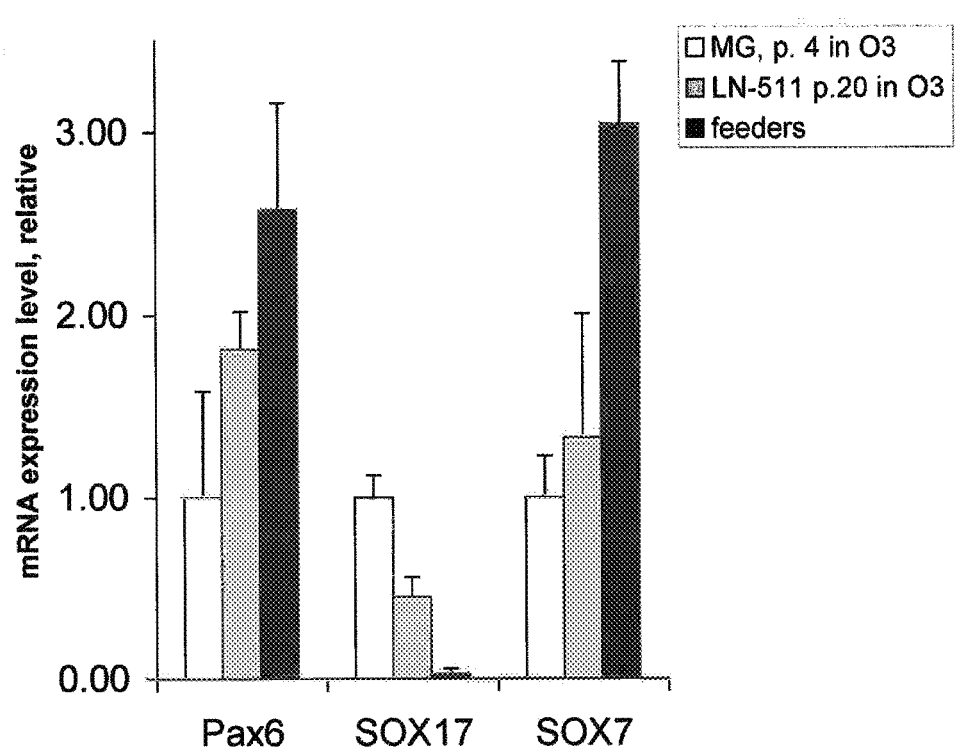
FIG. 12 is a graph showing levels of spontaneous differentiation in LN-511, Matrigel and feeder HS207 cell cultures. Real-time quantitative RT-PCR analysis was used to compare number of mRNA transcripts of differentiation markers Pax6, Sox17, and Sox7 in HS207 cells cultured on Matrigel in O3 medium (white bars), on LN-511 in O3 medium (grey bars) and on human foreskin fibroblast layer in a serum replacement based medium (black bars). Error bars show 95% confidence interval.

To assess the level of spontaneous differentiation in hES cultures on LN-511, Matrigel, and on feeders Applicants compared expression level of markers of differentiation Pax6, Sox17, and Sox7. Real-time quantitative RT-PCR revealed similar levels of expression of all three markers in LN-511 cultures after 20 passages (4 months) and Matrigel cultures after 4 passages (1 month) (FIG. 12).

Figure 13A:
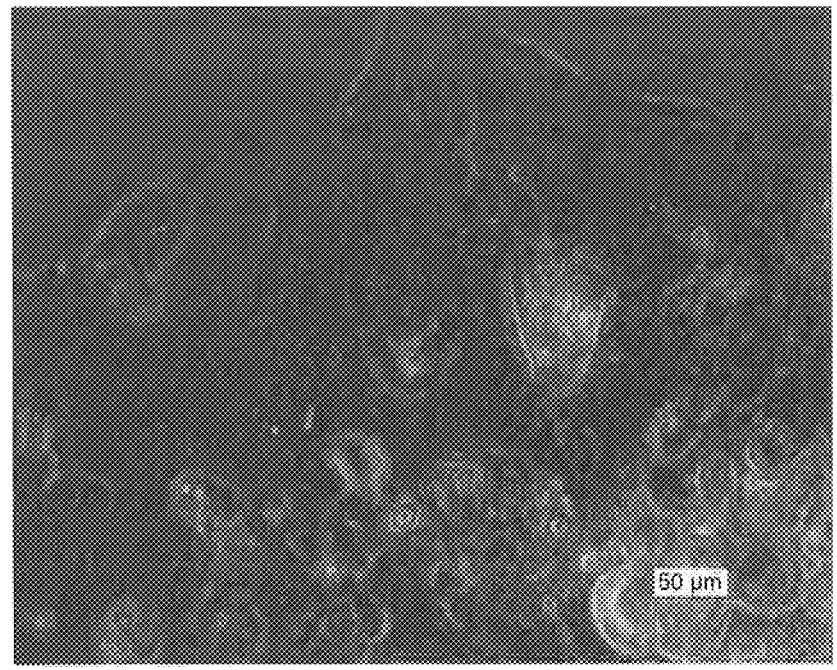
FIG. 13a shows morphologically typical hESC growing out from the inner cell mass of a day six blastocysts four days after mechanical isolation of the inner cell mass and plating on LN511.
Figures 13B, 13C:
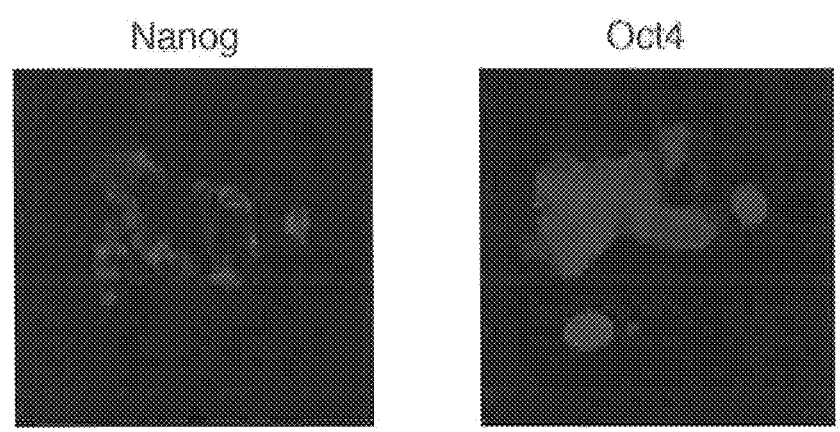
FIG. 13b shows immunostaining of HS588 cells with anti-Nanog antibodies at passage 2 on LN-511 in O3 medium.
FIG. 13c shows immunostaining of the same cells with anti-Oct4 antibodies.

To study if LN-511 could be useful for new hES cell line derivation Applicants isolated the inner cell mass of three day six blastocysts and plated them on LN-511. The cells readily attached to the coating and generated typical for hES cells outgrowth (FIG. 13a). After 10 days in culture the outgrowth was mechanically dissociated into pieces and part of it was immunostained showing expression of markers of pluripotency Nanog and Oct4 (FIGS. 13b and 13c). The experiments were performed in accordance with ethical committee approval.

E. Human ES Cells can Differentiate into all Three Germ Line Lineages of the Human Embryo after 4 Months in Culture on LN-511

HS207, HS420 and HS401 cells cultured for 15, 20 and 20 passages on LN-511 in O3 medium and HS207 cells cultured for 23 passages in H3 medium formed teratomas after being grafted into the testes of severe combined immunodeficient mice (SCID). Analysis of the stained sections confirmed the ability of the cells to differentiate into cells of all three germ lineages of the human embryo (FIGS. 7a-7d). To further examine the developmental potential, the cells of all three hES lines after 20 passages on LN-511 in O3 medium were examined in vitro by the formation of embryoid bodies and subsequent immunostaining on markers of all three embryonic germ layers. The staining revealed expression of mesoderm (smooth muscle actin), ectoderm (Nestin and MAP-2) and endoderm (α-fetoprotein) markers (FIG. 7e), thus providing additional evidence of pluripotency of the cells.

F. Different Human ES Cells Lines Self-Renew on LN-511.

Figure 8:
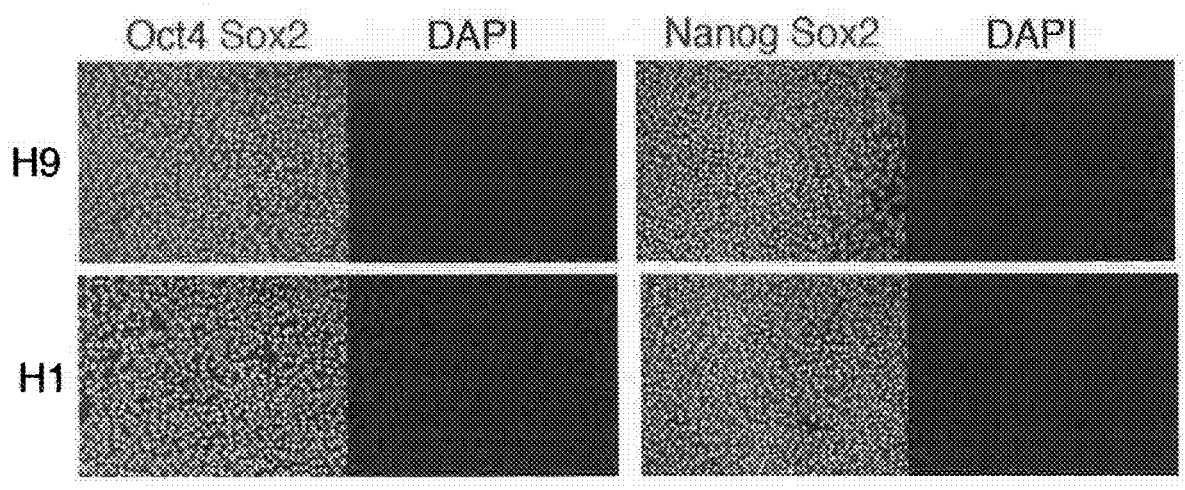
FIG. 8 shows immunoanalysis of different hES cells grown on LN-511.

To determine if LN-511 can support self-renewal of different hES lines, Applicants cultured well characterized and widely used H1 and H9 hES lines cultured on the protein in O3 or mTeSR1 medium. The H1 and H9 cells had phenotype and proliferation rate similar to that of HS207, HS420 and HS401 cells under the same conditions. Immunofluorescence analysis revealed that after 5 passages (1 month) in culture on LN-511, the H1 and H9 cells maintained expression of pluripotency markers, such as Oct4, Nanog, and Sox2 (FIG. 8).

III. Discussion

The present study demonstrated that LN-511 provided an artificial niche for supporting survival and self-renewal of human ES cells in culture in a xeno-free environment for at least 20 passages, or for 4 months. Importantly, the cells did form teratomas containing cell lineages of all three germ lineages of the human embryo after being cultured on LN-511 for that long period. Since there is a great need for a chemically defined xeno-free feeder free culture systems for hES cells, the system described here may provide a solution for that problem.

LN-511 is likely to be part of the natural niche for stem cells in the human embryo, as this protein has been detected in the inner cell mass of the blastocysts which is the natural origin of human ES cells. Furthermore, LN-511 is expressed in colonies of human embryonic stem cells cultured in vitro on feeder cells. Moreover, human ES cells express LN-511 themselves (FIG. 4c), and the protein promotes ES cells assembly, which is crucial for their self-renewal on a feeder layer. Since LN-511 is a part of the natural environment of hES cells, it can provide a biologically relevant coating matrix for self-renewal of human ES cell in vitro. It was recently reported that hES cells stayed pluripotent on several recombinant human laminins, such as LN-111, LN-332 and LN-511 for 96 hours. However, a previous study with mouse ES cells showed that it is important to culture the cells longer in order to demonstrate the capacity of the matrix molecules for ES cells self-renewal. In that study, mouse ES cells survived and proliferated on both LN-511 and LN-332 for at least 169 days, but only mouse ES cells cultured on LN-511 were able to generate germ-line competent chimeric mice.

It was interesting that the hES cells tended to form monolayers after being passaged in clumps to new LN-511 coated plates. This suggests that LN-511 could normally provide human ES cells with a migration potential, thus avoiding formation of dense multilayer clusters with poor transfer of soluble nutrients and growth factors. Availability of soluble factors for hES cells cultured on LN-511 can help to avoid spontaneous differentiation and mortality, which usually appears in the middle of overgrown ES cell colonies when cultured on feeders or Matrigel. Monolayers of hES cells could also be beneficial for development of differentiation procedures, since equal availability of soluble factors could create more homogeneous populations of differentiated cells.

Figure 6F:
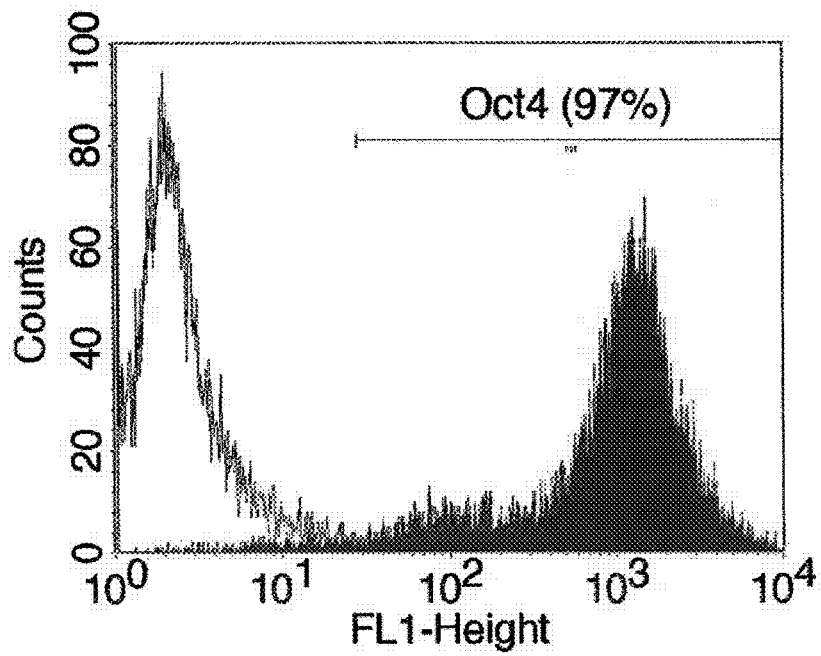
FIG. 6f shows FACS analysis of HS207 cells after 25 passages on LN-511 in O3 medium for cell surface marker of pluripotency Oct 4. The percentage of positive cells is listed in parentheses.
Figure 7E:
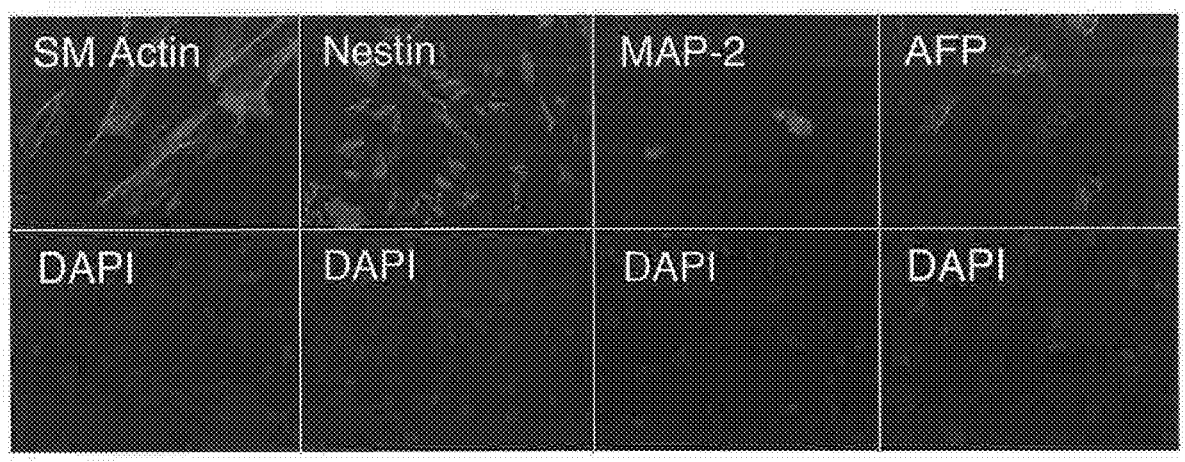
FIG. 7e shows immunostaining of embryoid bodies formed from HS207 cells after 20 passages on LN-511 revealed expression of markers for the three embryonic cell layers: smooth muscle actin (depicted as SM Actin), Nestin (Nestin), MAP-2 (MAP-2) and α-fetoprotein (AFP). Bottom panels are nuclear DAPI staining.

All populations of human ES cells contain some proportion of differentiated cells, probably due to spontaneous differentiation. An artificial niche should provide some competition advantages for non-differentiated human ES cells to colonize it and self-renew. Applicants did not perform any positive selection during the experiment, but nevertheless, Applicants showed using FACS that the proportion of undifferentiated human ES cells was stable and high throughout the whole experiment (FIG. 6f).

Applicants showed that the mechanism of human ES cells attachment to LN-511 was also strongly dependent on binding to α6β1 integrin receptor (FIG. 5a). Moreover, Applicants observed that antibodies against β1 integrin supported stronger attachment of the human ES cells than β2, β3 or β4 integrins, emphasizing the pivotal role of β1 containing integrins in cell adhesion (FIG. 5b). Recently, it has been shown that α6β1 is the most abundant integrin isoform on a hES cell surface24. Based on these observations, Applicants suggest that human ES cells abundantly expressing α6β1 integrins can attach fast and efficiently migrate on a LN-511 coated surface that, in turn, facilitates their self-renewal. Hence, the role of LN-511 could be to provide to human ES cells focal adhesion contacts to the surface and enable mobility on it. The fact that LN-511 expression is not restricted to the early embryos, but found in basement membranes of many adult tissues, supports that notion.

Time-wise, the present results obtained with human ES cell self-renewal on LN-511 coated laboratory plates, are at least as good as those obtained with the mouse EHS sarcoma-derived Matrigel or on human feeder cells. However, the completely defined and xeno-free composition of the human LN-511 coating can have a significant advantage from the point of view of standardized, non-varying scientific and future clinical applications. Also, a chemically defined substratum is a major advantage compared with using feeder cells for the same purpose, because feeder cells can vary in their production of bioactive molecules, such as cytokines, growth factors and other proteins are largely unknown, and they can also pose a risk for microbial and viral contamination, as well as batch-to-batch variability in the results. Thus, the LN-511 based xeno-free and feeder-free human ES cell culture system described in this study can be a significant solution for this problem. In most countries, regulatory authorities apply strict rules to any reagents that are intended for use in human therapy. Since human recombinant LN-511 is a chemically defined protein produced in human cells, it is feasible to establish a production protocol that can yield the protein suitable for the development of human cells for cell therapy. Manufacturing can be easily taken into a good manufacturing practice (GMP) laboratory.

The TeSR1 medium was formulated for use with Matrigel. It contains many growth factors in very high concentrations. Since LN-511 provided better spreading of hES cells and high average expression of the main pluripotency markers, it opens up for a possibility to optimize the medium composition in order to decrease the doses of the growth factors, especially bFGF. Unlike Matrigel, LN-511 is a defined homogeneous protein molecule that is stable from batch-to-batch coating. The use of a more defined environment to culture hES cells in vitro can help to develop and understand the molecular mechanism of differentiation and provide more controllable conditions for design of differentiation pathways for human ES cells in vitro.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for creating a new pluripotent human stem cell line in a defined and xeno-free environment comprising:
providing a substrate comprising a coating that is devoid of both animal proteins and feeder cells, and the coating comprises a single isoform of a full-length laminin consisting of laminin-511 (LN-511 or laminin-10);
plating cells from a blastocyst inner cell mass comprising pluripotent human stem cells onto the coating;
exposing the pluripotent human stem cells to a chemically defined medium that is devoid of feeder cells; and
obtaining a new pluripotent human stem cell line from outgrowth of the human stem cells.

2. The method of claim 1, wherein the new pluripotent human stem cell line is non-differentiated.

3. The method of claim 1, wherein the new pluripotent human stem cell line is homogeneous.

4. The method of claim 1, wherein the new pluripotent human stem cell line forms monolayers on the coating.

5. The method of claim 1, wherein the new pluripotent human stem cell line comprises non-differentiated embryonic stem cells.

6. The method of claim 1, further comprising:
harvesting the new pluripotent human stem cell line;
replating the new pluripotent human stem cell line on a second substrate comprising the coating;
exposing the new pluripotent human stem cell line to a chemically defined medium that is devoid of feeder cells; and
obtaining refined pluripotent human stem cells from outgrowth of the new pluripotent human stem cell line.

7. The method of claim 1, wherein the medium further comprises a growth factor.

8. A method for maintaining self-renewing pluripotent human stem cells, comprising:
a) providing a substrate comprising a coating that is devoid of both animal proteins and feeder cells, and the coating comprises only a single isoform of a laminin consisting of intact laminin-511 (LN-511 or laminin-10);
b) plating pluripotent human stem cells onto the coating;
c) exposing the pluripotent human stem cells to a chemically defined medium that is devoid of feeder cells, thereby maintaining self-renewing pluripotent human stem cells; and
d) periodically harvesting and replating the pluripotent human stem cells.

9. The method of claim 8, wherein the medium further comprises a growth factor.

10. The method of claim 8, wherein the pluripotent human stem cells from step c) form monolayers on the coating.

11. The method of claim 8, wherein the pluripotent human stem cells are non-differentiated embryonic stem cells.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Homo sapiens

<400> SEQUENCE: 1
cgaccatctg ccgctttgag                                           20

<210> SEQ ID NO 2
<211> LENGTH: 20
<212> TYPE: DNA

<213> ORGANISM: Homo sapiens

<400> SEQUENCE: 2 cccctgtcc cccattccta                                              20

<210> SEQ ID NO 3
<211> LENGTH: 26
<212> TYPE: DNA
<213> ORGANISM: Homo sapiens

<400> SEQUENCE: 3
agcatccgac tgtaaagaat cttcac                                      26

<210> SEQ ID NO 4
<211> LENGTH: 24
<212> TYPE: DNA
<213> ORGANISM: Homo sapiens

<400> SEQUENCE: 4
cggccagttg tttttctgcc acct                                        24

<210> SEQ ID NO 5
<211> LENGTH: 20
<212> TYPE: DNA
<213> ORGANISM: Homo sapiens

<400> SEQUENCE: 5
gaaggtgaag gtcggagtca                                             20

<210> SEQ ID NO 6
<211> LENGTH: 20
<212> TYPE: DNA
<213> ORGANISM: Homo sapiens

<400> SEQUENCE: 6
ttcacaccca tgacgaacat                                             20

<210> SEQ ID NO 7
<211> LENGTH: 22
<212> TYPE: DNA
<213> ORGANISM: Homo sapiens

<400> SEQUENCE: 7
aacagacaca gccctcacaa ac                                          22

<210> SEQ ID NO 8
<211> LENGTH: 23
<212> TYPE: DNA
<213> ORGANISM: Homo sapiens

<400> SEQUENCE: 8
cgggaacttg aactggaact gac                                         23

<210> SEQ ID NO 9
<211> LENGTH: 20
<212> TYPE: DNA
<213> ORGANISM: Homo sapiens

<400> SEQUENCE: 9
ctttgggctg ctcgctatga                                             20

<210> SEQ ID NO 10
<211> LENGTH: 20

```
<212> TYPE: DNA
<213> ORGANISM: Homo sapiens

<400> SEQUENCE: 10
tggcttggaa agttcgggtc                                                      20

<210> SEQ ID NO 11
<211> LENGTH: 20
<212> TYPE: DNA
<213> ORGANISM: Homo sapiens

<400> SEQUENCE: 11
gaaggtggat ctcaggtagc                                                      20

<210> SEQ ID NO 12
<211> LENGTH: 21
<212> TYPE: DNA
<213> ORGANISM: Homo sapiens

<400> SEQUENCE: 12
catctcattg gtgagctcct t                                                    21

<210> SEQ ID NO 13
<211> LENGTH: 24
<212> TYPE: DNA
<213> ORGANISM: Homo sapiens

<400> SEQUENCE: 13
ctcactttcc tccgcgttgc ttcc                                                 24

<210> SEQ ID NO 14
<211> LENGTH: 24
<212> TYPE: DNA
<213> ORGANISM: Homo sapiens

<400> SEQUENCE: 14
tgccctggtc tttgtccttc atcc                                                 24
```